United States Patent
Shimizu et al.

(10) Patent No.: US 8,188,299 B2
(45) Date of Patent: May 29, 2012

(54) ACRYLATE DERIVATIVES, ALCOHOL DERIVATIVES, AND METHOD FOR PRODUCING THEM

(75) Inventors: Kazuya Shimizu, Ibaraki (JP); Masayoshi Yamanaka, Okayama (JP); Tatsuhiko Hayashibara, Okayama (JP); Hideharu Iwasaki, Okayama (JP)

(73) Assignee: Kuraray Co., Ltd., Kurashiki-shi (JP)

( * ) Notice: Subject to any disclaimer, the term of this patent is extended or adjusted under 35 U.S.C. 154(b) by 0 days.

(21) Appl. No.: 12/884,677

(22) Filed: Sep. 17, 2010

(65) Prior Publication Data

US 2012/0071667 A1    Mar. 22, 2012

(51) Int. Cl.
*C07D 209/56* (2006.01)
(52) U.S. Cl. ........................................... 548/434
(58) Field of Classification Search .................. 548/434
See application file for complete search history.

(56) References Cited

OTHER PUBLICATIONS

Brown et al. (Canadian J. of Chem., 47 (1969), p. 2751-62).*

* cited by examiner

*Primary Examiner* — Robert Havlin

(74) *Attorney, Agent, or Firm* — Oblon, Spivak, McClelland, Maier & Neustadt, L.L.P.

(57) ABSTRACT

Provided are an acrylate derivative useful as a raw material of a polymer compound for resist compositions capable of giving resist patterns which are excellent in lithographic performance and have a good shape, an intermediate thereof (alcohol derivative) and production processes for them. To be specific, it is an acrylate derivative represented by a formula shown below:

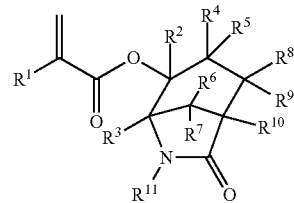

(wherein $R^1$ represents a hydrogen atom, methyl or trifluoromethyl; $R^2$, $R^3$, $R^5$, $R^7$, $R^8$, $R^9$ and $R^{10}$ each represent independently a hydrogen atom, an alkyl group having 1 to 6 carbon atoms, a cycloalkyl group having 3 to 6 carbon atoms or an alkoxy group having 1 to 6 carbon atoms; $R^4$ and $R^6$ each represent independently a hydrogen atom, an alkyl group having 1 to 6 carbon atoms, a cycloalkyl group having 3 to 6 carbon atoms or an alkoxy group having 1 to 6 carbon atoms, or both of $R^4$ and $R^6$ are combined to represent an alkylene group having 1 to 3 carbon atoms, —O— or —S—; and $R^{11}$ represents a hydrogen atom, an alkyl group having 1 to 6 carbon atoms or a cyclic hydrocarbon group having 3 to 10 carbon atoms).

3 Claims, No Drawings

ACRYLATE DERIVATIVES, ALCOHOL DERIVATIVES, AND METHOD FOR PRODUCING THEM

TECHNICAL FIELD

The present invention relates to an acrylate derivative, an alcohol derivative and production processes for the same.

BACKGROUND ART

A lithographic technology comprises, for example, a step in which a resist film comprising a resist material is formed on a substrate and in which the above resist film is selectively exposed to a radiated light such as light, an electron beam and the like via a mask having a prescribed pattern formed thereon and then subjected to developing treatment to thereby form a resist pattern of a prescribed form in the resist film described above. A resist material changed to a characteristic in which an exposed part is dissolved in a developer is called a positive type, and a resist material changed to a characteristic in which an exposed part is not dissolved in a developer is called a negative type.

In recent years, fining of patterns goes on rapidly by progress of a lithographic technology in production of semiconductor devices and liquid crystal display devices.

In general, a wavelength of an exposure light source is shortened (elevated in an energy) as a method for obtaining fine patterns. To be specific, a UV ray represented by a g-line and an i-line has so far been used therefor, but at present, semiconductor devices have been initiated to be commercially produced by using a KrF excimer laser and an ArF excimer laser. Further, a $F_2$ excimer laser having a shorter wavelength (higher energy) than those of a KrF excimer laser and an ArF excimer laser, an electron beam, EUV (an extreme UV ray) and an X ray are investigated.

Lithographic performance such as a sensitivity to the above exposure light sources and a resolution in which patterns having a fine dimension can be reproduced are required to resist materials.

Chemical amplification type resist compositions comprising a base material component in which a solubility to an alkali developer is changed by an action of acid and an acid-generating agent component generating acid by exposure are used as a resist material satisfying the above requirement.

A composition comprising a resin component (base resin) in which a solubility to an alkali developer is increased by an action of acid and an acid-generating agent component is usually used as a chemical amplification type resist composition of a positive type. In a resist film formed by using the above resist composition, acid is generated from the acid-generating agent component in an exposed part by subjecting it to selective exposure in forming a resist pattern, and a solubility of the resin component to an alkali developer is increased by an action of the above acid to make the exposed part soluble in the alkali developer.

At present, resins (acryl base resins) having a structural unit derived from (meth)acrylate in a main chain are usually used as a base resin for resists used in ArF excimer laser lithography and the like because they are excellent in a transparency in the vicinity of 193 nm (refer to, for example, a patent document 1).

Further, chemical amplification type resist compositions are formulated with, for example, nitrogen-containing organic compounds such as alkylamines, alkylalcoholamines and the like in addition to a base resin and an acid-generating agent. The above nitrogen-containing organic compound acts as a quencher for trapping acid generated from an acid-generating agent and contributes to enhancing lithographic performance such as a shape of a resist pattern and the like.

In general, tertiary amines are widely used as the above nitrogen-containing organic compound at present. Further, various nitrogen-containing organic compounds are used in order to enhance a process margin and the like in forming an isolated pattern as fining of patterns is advanced (refer to, for example, patent documents 2 and 3).

Patent document 1: Japanese Patent Application Laid-Open No. 241385/2003
Patent document 2: Japanese Patent Application Laid-Open No. 166476/2001
Patent document 3: Japanese Patent Application Laid-Open No. 215689/2001

DISCLOSURE OF THE INVENTION

Problems to be Solved by the Invention

While lithographic technologies are expected to be advanced further more and expanded in the application fields in the future, novel materials which can be used for lithographic applications are required to be developed. For example, resist materials by which various lithographic performance such as a resolution, a depth of focus (DOF), a line width roughness (LWR), a critical dimensional uniformity (CDU) and the like and a pattern shape (for example, a rectangularity in a case of a line pattern and a circularity in a case of a hole pattern) are improved more than ever are demanded as fining of patterns is advanced.

However, in resist compositions prepared by using tertiary amines as nitrogen-containing organic compounds, while controlling diffusion of acid from an exposed area to an unexposed area and an effect of an environmental durability are observed, they are reacted with ester parts in an acid-generating agent or a base material component contained in a resist composition because of a high nucleophilicity and a high basicity to bring about decomposition, and therefore the problems that the storage stability is low and that the lithographic performance are lowered as well are involved therein.

Resist compositions containing the nitrogen-containing organic compounds described in the patent documents 2 and 3 have not yet been able to satisfy the lithographic performance and the pattern shape required as fining of patterns is advanced.

The present invention has been made in light of the situations described above, and an object thereof is to provide an acrylate derivative useful as a raw material of a polymer compound for resist compositions capable of giving resist patterns which are excellent in lithographic performance and have a good shape, an intermediate thereof (alcohol derivative) and production processes for them.

Means for Solving the Problems

Intense investigations carried out by the present inventors have resulted in finding that the problems described above can be solved by using as a base resin, a polymer compound obtained by polymerizing an acrylate derivative having a specific nitrogen atom-containing group as a quencher for trapping acid generated from an acid-generating agent, and thus they have come to complete the present invention.

That is, the present invention provides the inventions of [1] to [5] described below.

[1] An acrylate derivative (hereinafter referred to as an acrylate derivative (1)) represented by Formula (1) shown below:

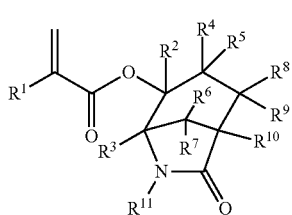

(wherein $R^1$ represents a hydrogen atom, methyl or trifluoromethyl; $R^2$, $R^3$, $R^5$, $R^7$, $R^8$, $R^9$ and $R^{10}$ each represent independently a hydrogen atom, an alkyl group having 1 to 6 carbon atoms, a cycloalkyl group having 3 to 6 carbon atoms or an alkoxy group having 1 to 6 carbon atoms; $R^4$ and $R^6$ each represent independently a hydrogen atom, an alkyl group having 1 to 6 carbon atoms, a cycloalkyl group having 3 to 6 carbon atoms or an alkoxy group having 1 to 6 carbon atoms, or both of $R^4$ and $R^6$ are combined to represent an alkylene group having 1 to 3 carbon atoms, —O— or —S—; and $R^{11}$ represents a hydrogen atom, an alkyl group having 1 to 6 carbon atoms or a cyclic hydrocarbon group having 3 to 10 carbon atoms).

[2] A production process for the acrylate derivative (1), characterized by esterifying an alcohol derivative (hereinafter referred to as an alcohol derivative (2)) represented by Formula (2) shown below:

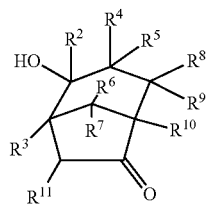

(wherein $R^2$, $R^3$, $R^4$, $R^5$, $R^6$, $R^7$, $R^8$, $R^9$, $R^{10}$ and $R^{11}$ are the same as defined above).

[3] An alcohol derivative.

[4] A production process for the alcohol derivative (2), characterized by oxidizing a cyclohexene derivative (hereinafter referred to as a cyclohexene derivative (3)) represented by Formula (3) shown below in the presence of a base:

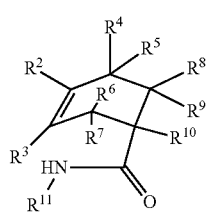

(wherein $R^2$, $R^3$, $R^4$, $R^5$, $R^6$, $R^7$, $R^8$, $R^9$, $R^{10}$ and $R^{11}$ are the same as defined above) to obtain an epoxy derivative (hereinafter referred to as an epoxy derivative (4)) represented by Formula (4) shown below:

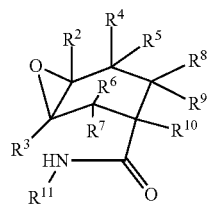

(wherein $R^2$, $R^3$, $R^4$, $R^5$, $R^6$, $R^7$, $R^8$, $R^9$, $R^{10}$ and $R^{11}$ are the same as defined above) and subjecting the above epoxy derivative (4) obtained to base treatment.

[5] A production process for the epoxy derivative (4), characterized by oxidizing the cyclohexene derivative (3) in the presence of a base.

Effect of the Invention

According to the present invention, capable of being provided are an acrylate derivative useful as a raw material of a polymer compound for resist compositions giving resist patterns which are excellent in lithographic performance and have a good shape, an intermediate thereof (alcohol derivative) and production processes for them.

BEST MODE FOR CARRYING OUT THE INVENTION

Acrylate derivative (1):

The following acrylate derivative (1) is useful for obtaining a resist composition giving resist patterns which are excellent in lithographic performance and have a good shape:

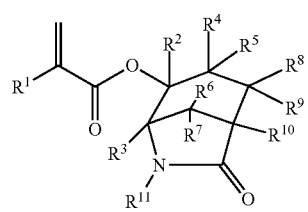

$R^1$ in the acrylate derivative (1) described above represents a hydrogen atom, methyl or trifluoromethyl. Among them, $R^1$ is preferably a hydrogen atom or methyl.

$R^2$, $R^3$, $R^5$, $R^7$, $R^8$, $R^9$ and $R^{10}$ in the acrylate derivative (1) described above each represent independently a hydrogen atom, an alkyl group having 1 to 6 carbon atoms, a cycloalkyl group having 3 to 6 carbon atoms or an alkoxy group having 1 to 6 carbon atoms.

$R^4$ and $R^6$ in the acrylate derivative (1) described above each represent independently a hydrogen atom, an alkyl group having 1 to 6 carbon atoms, a cycloalkyl group having 3 to 6 carbon atoms or an alkoxy group having 1 to 6 carbon atoms, or both of $R^4$ and $R^6$ are combined to represent an alkylene group having 1 to 3 carbon atoms, —O— or —S—.

$R^{11}$ in the acrylate derivative (1) described above represents a hydrogen atom, an alkyl group having 1 to 6 carbon atoms or a cyclic hydrocarbon group having 3 to 10 carbon atoms.

The alkyl groups having 1 to 6 carbon atoms each represented independently by $R^2$, $R^3$, $R^4$, $R^5$, $R^6$, $R^7$, $R^8$, $R^9$ and $R^{10}$ may be either linear or branched and include, for example, methyl, ethyl, n-propyl, isopropyl, n-butyl, isobutyl, s-butyl, n-pentyl, n-hexyl and the like. Among them, the alkyl groups having 1 to 3 carbon atoms are preferred from the viewpoint of obtaining a resist composition which gives a resist pattern having a good shape, and methyl is more preferred.

The cycloalkyl groups having 3 to 6 carbon atoms each represented independently by $R^2$, $R^3$, $R^4$, $R^5$, $R^6$, $R^7$, $R^8$, $R^9$ and $R^{10}$ include cyclopropyl, cyclobutyl, cyclopentyl and cyclohexyl.

The alkoxy groups having 1 to 6 carbon atoms each represented independently by $R^2$, $R^3$, $R^4$, $R^5$, $R^6$, $R^7$, $R^8$, $R^9$ and $R^{10}$ may be either linear or branched and include, for example, methoxy, ethoxy, propoxy, isopropoxy, n-butoxy, isobutoxy, t-butoxy, n-pentyloxy, n-hexyloxy and the like. Among them, the alkoxy groups having 1 to 3 carbon atoms are preferred from the viewpoint of obtaining a resist composition which gives a resist pattern having a good shape, and methoxy is more preferred.

Among the above groups, $R^2$, $R^3$, $R^5$, $R^7$, $R^8$, $R^9$ and $R^{10}$ are preferably a hydrogen atom or an alkyl group having 1 to 6 carbon atoms, and all of them are more preferably a hydrogen atom.

The alkylene group having 1 to 3 carbon atoms formed by combining $R^4$ with $R^6$ includes methylene, ethane-1,1-diyl, ethane-1,2-diyl, propane-1,1-diyl, propane-1,2-diyl and propane-1,3-diyl. Among them, methylene and ethane-1,2-diyl are preferred from the viewpoint of obtaining a resist composition which gives a resist pattern having a good shape, and methylene is more preferred.

Among the above groups, both of $R^4$ and $R^6$ are preferably a hydrogen atom, or both of them are preferably combined to represent an alkylene group having 1 to 3 carbon atoms or —O—, and they are more preferably methylene or —O—.

The alkyl group having 1 to 6 carbon atoms represented by $R^{11}$ may be either linear or branched and includes, for example, methyl, ethyl, n-propyl, isopropyl, n-butyl, isobutyl, s-butyl, t-butyl, n-pentyl, n-hexyl and the like. Among them, the alkyl group having 1 to 4 carbon atoms is preferred from the viewpoint of obtaining a resist composition which gives a resist pattern having a good shape, and it is preferably the branched alkyl group having 3 or 4 carbon atoms and more preferably t-butyl.

The cyclic hydrocarbon groups having 3 to 10 carbon atoms each represented independently by $R^{11}$ include cyclopropyl, cyclobutyl, cyclopentyl, cyclohexyl, adamantane-1-yl and the like.

Among the above groups, $R^{11}$ is preferably a hydrogen atom, methyl, ethyl, n-propyl, isopropyl, n-butyl, isobutyl, s-butyl, t-butyl and adamantane-1-yl from the viewpoint of obtaining a resist composition which gives a resist pattern having a good shape.

$R^1$, $R^2$, $R^3$, $R^4$, $R^5$, $R^6$, $R^7$, $R^8$, $R^9$, $R^{10}$ and $R^{11}$ in the acrylate derivative (1) each are the same as those in the alcohol derivative (2), the cyclohexene derivative (3) and the epoxy derivative (4) and those in a diene derivative (5), an acrylic halide derivative (6) and an amine derivative (7) which shall be described later.

The specific examples of the acrylate derivative (1) of the present invention shall be shown below, but it shall not specifically be restricted to them.

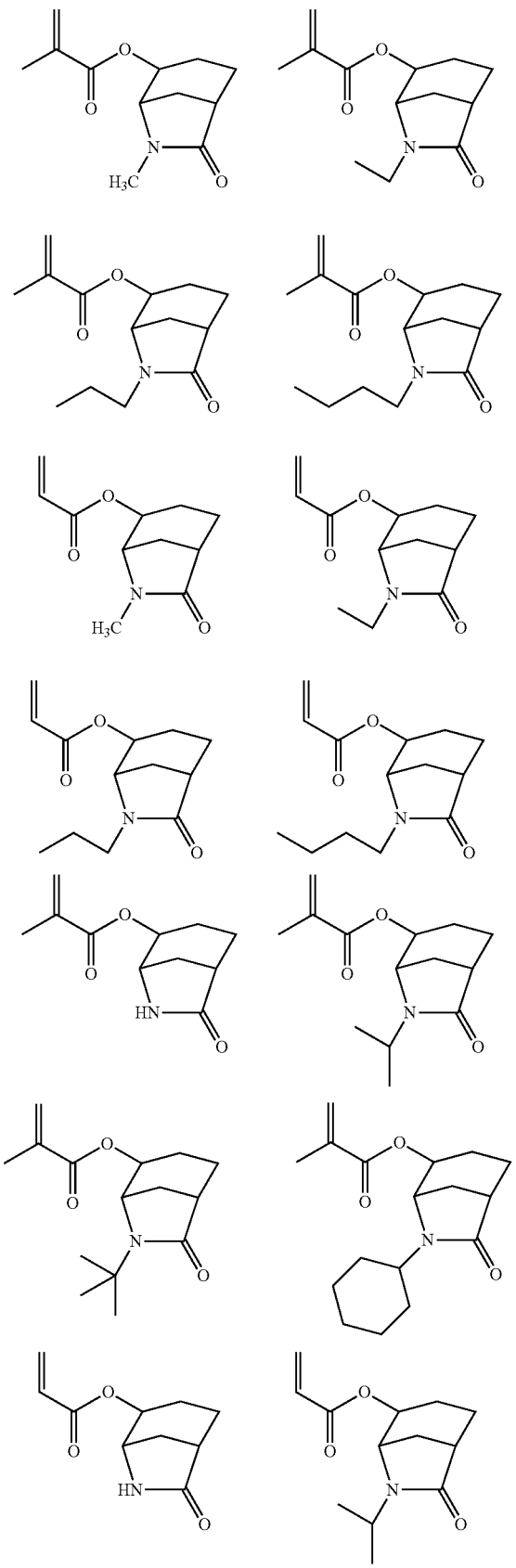

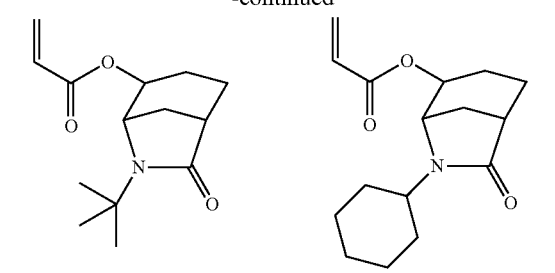
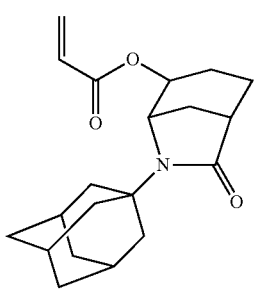
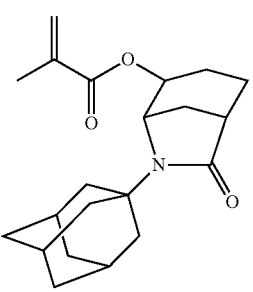
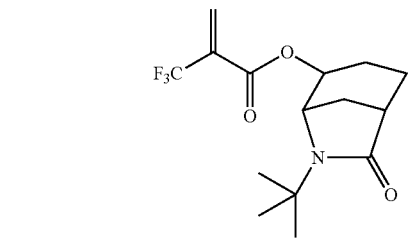
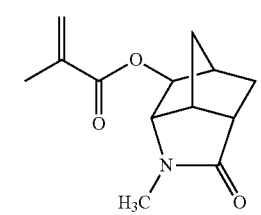
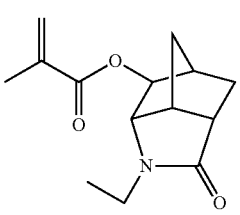
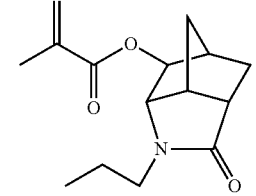
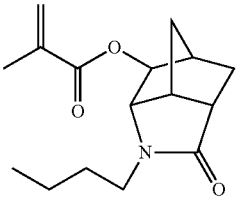
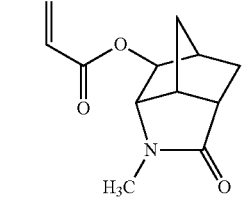
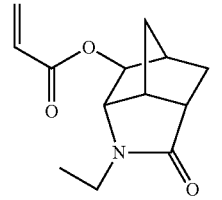
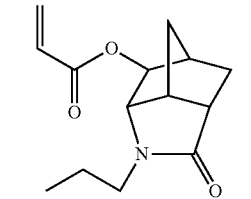
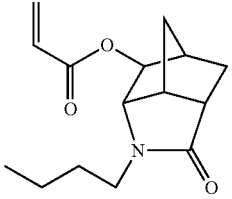
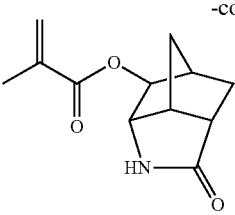
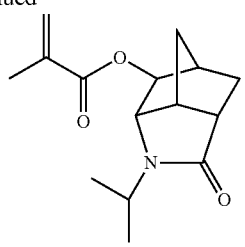
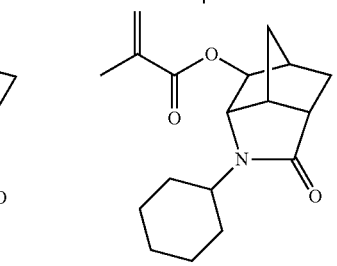
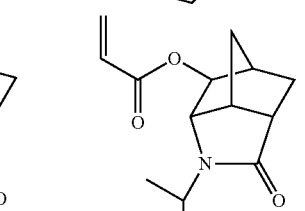
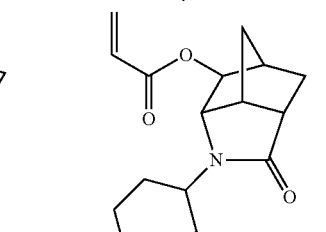
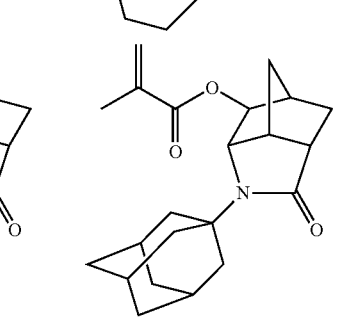
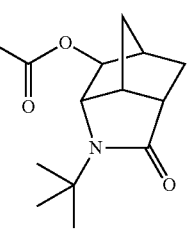
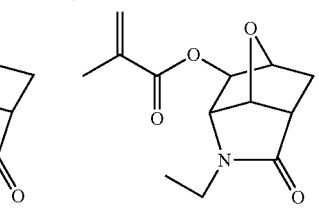

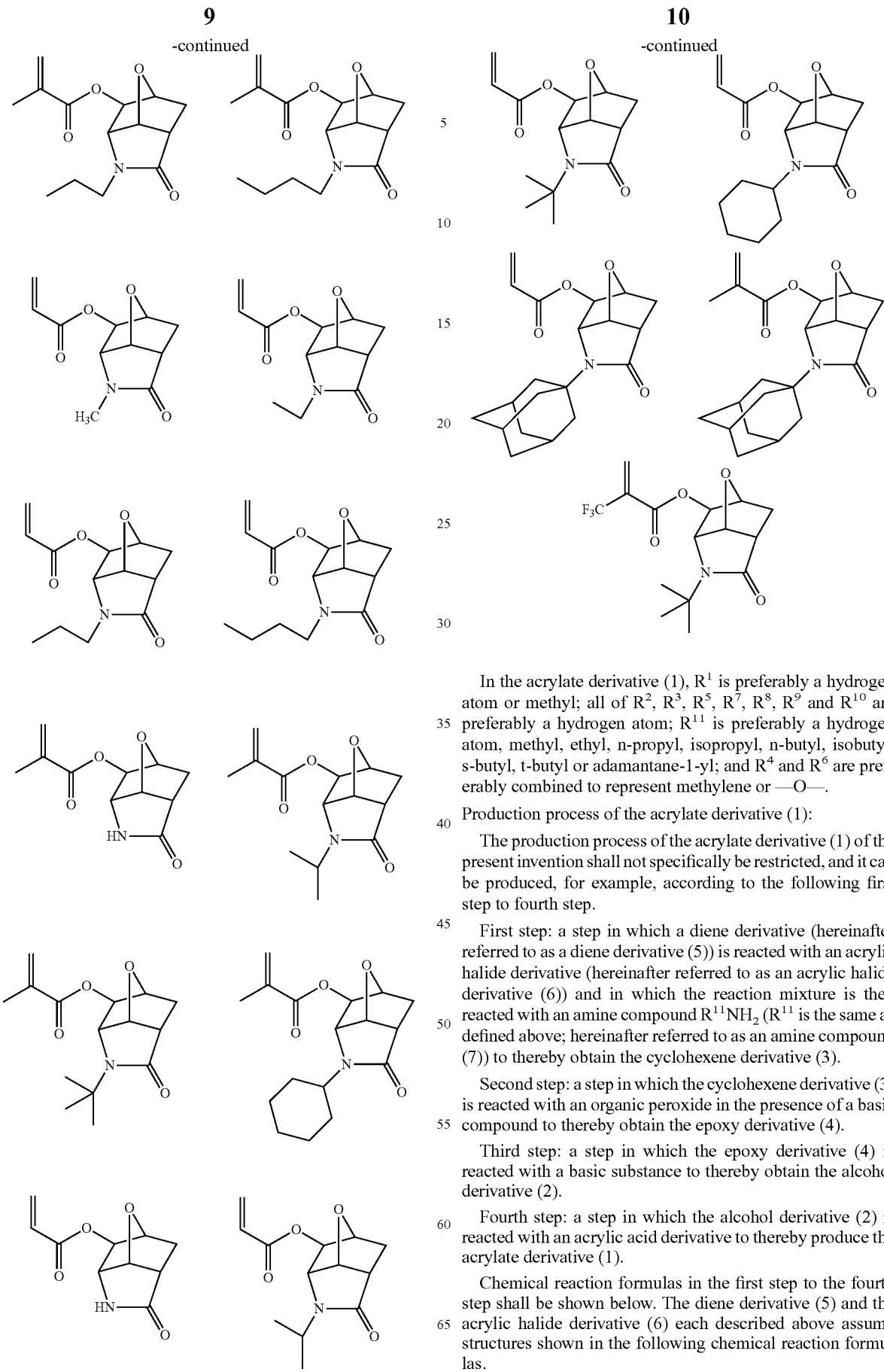

In the acrylate derivative (1), $R^1$ is preferably a hydrogen atom or methyl; all of $R^2$, $R^3$, $R^5$, $R^7$, $R^8$, $R^9$ and $R^{10}$ are preferably a hydrogen atom; $R^{11}$ is preferably a hydrogen atom, methyl, ethyl, n-propyl, isopropyl, n-butyl, isobutyl, s-butyl, t-butyl or adamantane-1-yl; and $R^4$ and $R^6$ are preferably combined to represent methylene or —O—.

Production process of the acrylate derivative (1):

The production process of the acrylate derivative (1) of the present invention shall not specifically be restricted, and it can be produced, for example, according to the following first step to fourth step.

First step: a step in which a diene derivative (hereinafter referred to as a diene derivative (5)) is reacted with an acrylic halide derivative (hereinafter referred to as an acrylic halide derivative (6)) and in which the reaction mixture is then reacted with an amine compound $R^{11}NH_2$ ($R^{11}$ is the same as defined above; hereinafter referred to as an amine compound (7)) to thereby obtain the cyclohexene derivative (3).

Second step: a step in which the cyclohexene derivative (3) is reacted with an organic peroxide in the presence of a basic compound to thereby obtain the epoxy derivative (4).

Third step: a step in which the epoxy derivative (4) is reacted with a basic substance to thereby obtain the alcohol derivative (2).

Fourth step: a step in which the alcohol derivative (2) is reacted with an acrylic acid derivative to thereby produce the acrylate derivative (1).

Chemical reaction formulas in the first step to the fourth step shall be shown below. The diene derivative (5) and the acrylic halide derivative (6) each described above assume structures shown in the following chemical reaction formulas.

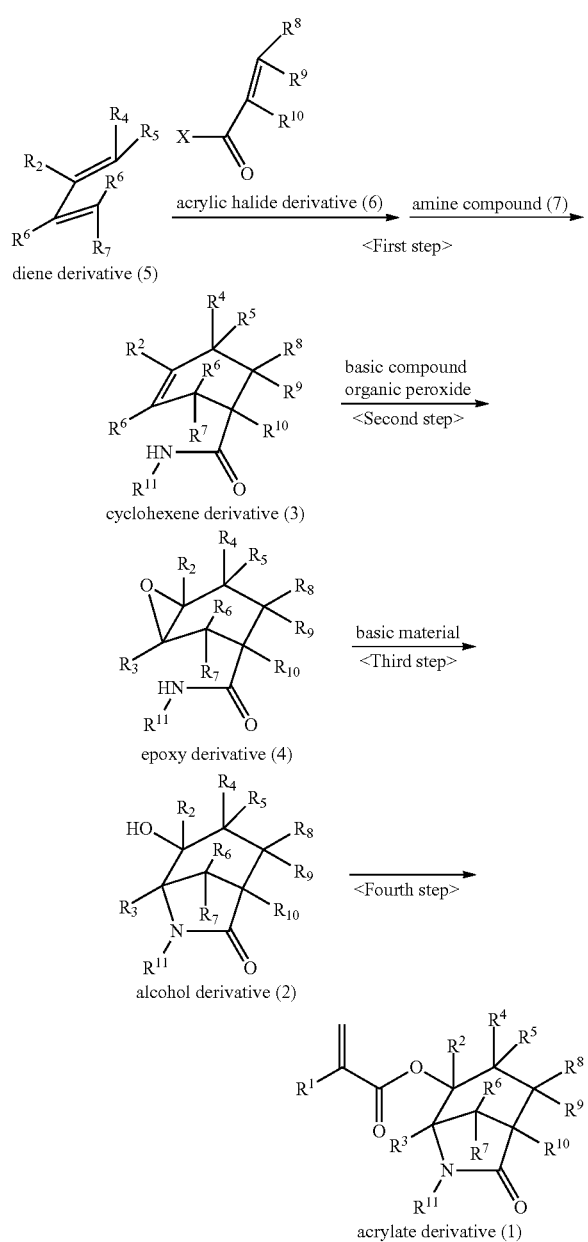

(wherein $R^1$, $R^2$, $R^3$, $R^4$, $R^5$, $R^6$, $R^7$, $R^8$, $R^9$, $R^{10}$ and $R^{11}$ are the same as defined above, and X represents a chlorine atom, a bromine atom or an iodine atom).

<First Step>

First, the first step in the production process for the cyclohexene derivative (3) shall be explained.

The first step comprises a step in which the diene derivative (5) is reacted with the acrylic halide derivative (6) (hereinafter referred to as a first step-1) and a step in which a reaction intermediate obtained in the first step-1 is reacted with the amine compound (7) (hereinafter referred to as a first step-2).

First Step-1:

The specific examples of the diene derivative (5) used in the first step-1 include butadiene, isoprene, 2,3-dimethylbutadiene, cyclopentadiene, furan and the like.

The specific examples of the acrylic halide derivative (6) used in the first step-1 include acrylic chloride, methacrylic chloride, acrylic bromide, methacrylic bromide, crotonic chloride, crotonic bromide, 3-methyl-2-butenoic chloride and the like.

A use amount of the diene derivative (5) falls in a range of preferably 1 to 50 times mole based on the acrylic halide derivative (6), and it falls in a range of more preferably 1 to 10 times mole from the viewpoint of easiness in after-treatment.

The reaction of the first step-1 is carried out in the presence or the absence of a solvent.

The solvent shall not specifically be restricted as long as the reaction is not inhibited, and it includes, for example, saturated hydrocarbon solvents such as hexane, heptane, cyclohexane and the like; aromatic hydrocarbon solvents such as benzene, toluene, xylene and the like; chlorinated hydrocarbon solvents such as methylene chloride, dichloroethane, chloroform, chlorinated benzene and the like; ether solvents such as diethyl ether, diisopropyl ether, tetrahydrofuran, furan and the like; and ester solvents such as methyl acetate, ethyl acetate, propyl acetate and the like. The solvent may be used alone or in a mixture of two or more kinds thereof.

When the reaction is carried out in the presence of the solvent, a use amount of the solvent falls in a range of preferably 0.5 to 100 mass times based on the diene derivative (5), and it falls in a range of more preferably 0.5 to 20 mass times from the viewpoint of easiness in after-treatment.

A reaction temperature in the first step-1 falls, though varied depending on the kinds of the diene derivative (5) and the acrylic halide derivative (6), in a range of preferably −30 to 100° C., more preferably −10 to 50° C. The reaction pressure shall not specifically be restricted, and the reaction is preferably carried out usually under an atmospheric pressure.

A reaction time in the first step-1 falls, though varied depending on the kinds and the use amounts of the diene derivative (5) and the acrylic halide derivative (6) and the reaction temperature, in a range of preferably about 1 to 50 hours.

The reaction in the first step-1 is preferably carried out under inert gas atmosphere of nitrogen, argon and the like.

The reaction mixture containing the reaction intermediates obtained in the first step-1 can be used as it is for a raw material in the first step-2 without carrying out specifically refining operation, and it is preferably used in the above manner.

A method for carrying out the first step-1 shall not specifically be restricted, and preferred is a method in which a reactor is charged with the acrylic halide derivative (6) and, if desired, a solvent and in which the diene derivative (5) is dropwise added to the above mixed solution under a desired reaction temperature and a desired reaction pressure.

First Step-2:

The specific examples of the amine compound (7) used in the first step-2 include ammonia, methylamine, ethylamine, n-propylamine, isopropylamine, n-butylamine, isobutylamine, s-butylamine, t-butylamine, cyclopropylamine, cyclohxylamine, 1-adamantylamine and the like.

A use amount of the amine compound (7) falls in a range of preferably 1 to 10 times mole based on the acrylic halide derivative (6) used in the first step-1, and it falls in a range of more preferably 1 to 5 times mole from the viewpoint of easiness in after-treatment. A use form of the amine compound (7) shall not specifically be restricted, and it may be used in the form of an aqueous solution or may be used as it is.

The reaction of the first step-2 is carried out in the presence or the absence of a solvent.

The solvent shall not specifically be restricted as long as the reaction is not inhibited, and it includes the same solvents as shown as the examples in the explanation of the first step-1. Accordingly, the solvent used when the solvent is used in the first step-1 is used preferably as it is in the first step-2. The solvent may be used alone or in a mixture of two or more kinds thereof.

When the reaction is carried out in the presence of the solvent, a use amount of the solvent falls in a range of preferably 0.5 to 100 mass times based on the diene derivative (5) used in the first step-1, and it falls in a range of more preferably 0.5 to 20 mass times from the viewpoint of easiness in after-treatment.

When the reaction mixture obtained in the first step-1 is used as it is for a raw material in the first step-2, an amount of the solvent may be as it is, or it may be further added.

A reaction temperature in the first step-2 falls, though varied depending on the kinds of the amine compound (7) and the acrylic halide derivative (6), in a range of preferably −30 to 100° C., more preferably −10 to 50° C. The reaction pressure shall not specifically be restricted, and the reaction is preferably carried out usually under an atmospheric pressure.

A reaction time in the first step-2 falls, though varied depending on the kinds and the use amounts of the amine compound (7) and the acrylic halide derivative (6) and the reaction temperature, in a range of preferably about 1 to 50 hours.

The reaction in the first step-2 is preferably carried out under inert gas atmosphere of nitrogen, argon and the like.

A method for carrying out the first step-2 shall not specifically be restricted, and preferred is a method in which a reactor is charged with the amine compound (7) and, if desired, a solvent and in which the reaction intermediate obtained in the first step-1 is dropwise added to the above mixed solution under a desired reaction temperature and a desired reaction pressure.

The cyclohexene derivative (3) can be separated from the reaction mixture obtained by the method described above and refined by a method used usually for separating and purifying organic compounds.

For example, after finishing the reactions in the first step-2, an organic solvent and water are added to the reaction solution and then left standing still to separate the mixture into an organic layer and an aqueous layer, and the organic layer is concentrated, whereby the cyclohexene derivative can be separated. Then, it is refined, if necessary, by recrystallization, silica gel chromatography and the like, whereby the cyclohexene derivative (3) having a high purity can be obtained.

<Second Step>

Next, the second step in the production process for the epoxy derivative (4) shall be explained.

The specific examples of the organic peroxide used in the second step include peracetic acid, m-chloroperbenzoic acid, dimethyldioxirane and the like.

A use amount of the organic peroxide falls in a range of preferably 1 to 10 times mole based on the cyclohexene derivative (3), and it falls in a range of more preferably 1 to 5 times mole from the viewpoint of easiness in after-treatment.

The specific examples of the basic compound used in the second step include alkali metal hydroxides such as sodium hydroxide, potassium hydroxide and the like; alkali metal carbonates such as sodium carbonate, potassium carbonate and the like; alkali earth metal hydroxides such as calcium hydroxide, barium hydroxide and the like; and alkali earth metal carbonates such as calcium carbonate, barium carbonate and the like. Among them, the alkali metal carbonates are preferred.

A use amount of the basic compound falls in a range of preferably 1 to 20 times mole based on the organic peroxide, and it falls in a range of more preferably 1 to 10 times mole from the viewpoint of easiness in after-treatment.

The reaction of the second step is carried out usually in the presence of a solvent.

The solvent shall not specifically be restricted as long as the reaction is not inhibited, and it includes, for example, water; saturated hydrocarbon solvents such as hexane, heptane, cyclohexane and the like; aromatic hydrocarbon solvents such as benzene, toluene, xylene and the like; chlorinated hydrocarbon solvents such as methylene chloride, dichloroethane, chlorinated benzene and the like; and ester solvents such as methyl acetate, ethyl acetate, isopropyl acetate and the like. The solvent may be used alone or in a mixture of two or more kinds thereof.

A use amount of the solvent falls in a range of preferably 0.5 to 100 mass times based on the cyclohexene derivative (3), and it falls in a range of more preferably 0.5 to 20 mass times from the viewpoint of easiness in after-treatment.

A reaction temperature in the second step falls, though varied depending on the kinds of the organic peroxide and the cyclohexene derivative (3), in a range of preferably −80 to 100° C., more preferably −30 to 50° C. The reaction pressure shall not specifically be restricted, and the reaction is preferably carried out usually under an atmospheric pressure.

A reaction time in the second step falls, though varied depending on the kinds and the use amounts of the organic peroxide and the cyclohexene derivative (3) and the reaction temperature, in a range of preferably about 1 to 50 hours.

The reaction in the second step is preferably carried out under inert gas atmosphere of nitrogen, argon and the like.

The reaction in the second step can be terminated by adding a reducing agent.

The reducing agent includes, for example, sodium sulfite, sodium thiosulfate, sodium hydrogensulfite and the like.

When the reaction in the second step is terminated by adding the reducing agent, an addition amount of the above reducing agent falls in a range of preferably 1 to 5 times mole based on the unreacted organic peroxide, and it falls in a range of more preferably 1 to 3 times mole from the viewpoint of easiness in after-treatment.

A method for carrying out the second step shall not specifically be restricted, and preferred is a method in which a reactor is charged with the cyclohexene derivative (3), the basic compound and the solvent and in which a mixed solution of the organic peroxide and the solvent is dropwise added to the above mixed solution under a desired reaction temperature and a desired reaction pressure.

The epoxy derivative (4) can be separated from the reaction mixture obtained by the method described above and purified by a method used usually for separating organic compounds, such as extraction by a solvent, distillation and the like. Further, a purity thereof can be enhanced by a method used usually for purifying organic compounds, such as recrystallization, distillation, sublimation and the like.

<Third Step>

Next, the third step in the production process for the alcohol derivative (2) shall be explained.

The specific examples of the basic substance used in the third step include alkali metal alkoxides such as sodium methoxide, sodium ethoxide, potassium methoxide, potassium ethoxide, sodium t-butoxide, potassium t-butoxide and the like; and alkali metal hydrides such as lithium hydride, sodium hydride, potassium hydride and the like. Among them, sodium t-butoxide, potassium t-butoxide and sodium hydride are preferred.

A use amount of the basic substance falls in a range of preferably 1 to 5 times mole based on the epoxy derivative (4), and it falls in a range of more preferably 1 to 3 times mole from the viewpoint of easiness in after-treatment.

The third step is carried out usually in the presence of a solvent.

The solvent shall not specifically be restricted as long as the reaction is not inhibited, and it includes, for example, saturated hydrocarbon solvents such as hexane, heptane, cyclohexane and the like; aromatic hydrocarbon solvents such as benzene, toluene, xylene and the like; ether solvents such as diethyl ether, diisopropyl ether, tetrahydrofuran and the like; and alcohol solvents such as methanol, ethanol, t-butanol and the like. The solvent may be used alone or in a mixture of two or more kinds thereof.

A use amount of the solvent falls in a range of preferably 0.5 to 100 mass times based on the epoxy derivative (4), and it falls in a range of more preferably 0.5 to 20 mass times from the viewpoint of easiness in after-treatment.

A reaction temperature in the third step falls, though varied depending on the kinds of the basic substance and the epoxy derivative (4), in a range of preferably −80 to 100° C., more preferably −30 to 50° C. The reaction pressure shall not specifically be restricted, and the reaction is preferably carried out usually under an atmospheric pressure.

A reaction time in the third step falls, though varied depending on the kinds and the use amounts of the basic substance and the epoxy derivative (4) and the reaction temperature, in a range of preferably about 1 to 50 hours.

The reaction in the third step is preferably carried out under inert gas atmosphere of nitrogen, argon and the like.

The reaction in the third step can be terminated by adding water.

When the reaction in the third step is terminated by adding water, an addition amount of water falls in a range of preferably 1 to 100 times mole based on the basic substance used, and it falls in a range of more preferably 1 to 50 times mole from the viewpoint of easiness in after-treatment.

A method for carrying out the third step shall not specifically be restricted, and preferred is a method in which a reactor is charged with the basic substance and the solvent and in which the epoxy derivative (4) is slowly added to the above mixed solution under a desired reaction temperature and a desired reaction pressure.

The alcohol derivative (2) can be separated from the reaction mixture obtained by the method described above and purified by a method used usually for separating organic compounds, such as extraction by a solvent, distillation and the like. Further, a purity thereof can be enhanced by a method used usually for purifying organic compounds, such as recrystallization, distillation, sublimation and the like.

The specific examples of the alcohol derivative (2) of the present invention obtained in the third step shall be shown below, but it shall specifically be restricted to them.

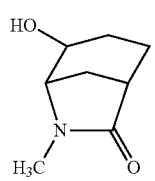 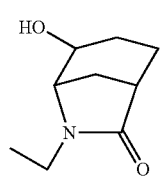 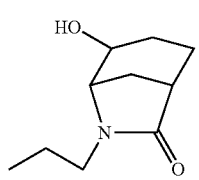

-continued

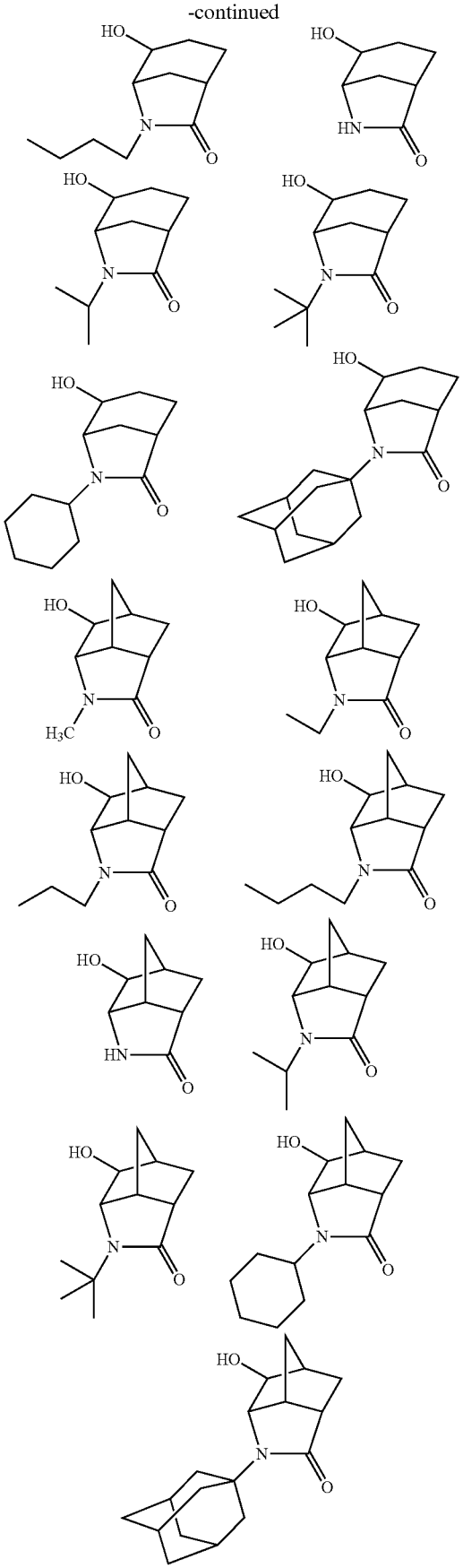

-continued

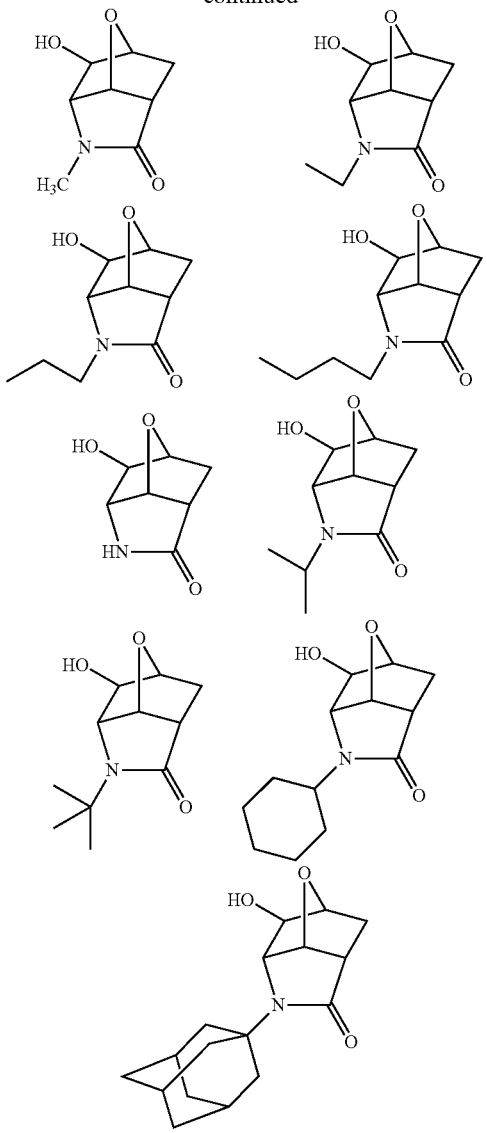

<Fourth Step>

Next, the fourth step in the production process for the acrylate derivative (1) shall be explained.

The acrylate derivative (1) is obtained by esterifying the alcohol derivative (2). A method for esterifying the alcohol derivative (2) shall not specifically be restricted and includes, for example, a method shown below.

Method 1: a method in which acrylic halides are reacted with the alcohol derivative (2) in the presence of a base.
Method 2: a method in which acrylic anhydrides are reacted with the alcohol derivative (2) in the presence of a base.
Method 3: a method in which acrylic acids are reacted with the alcohol derivative (2).

The respective methods 1 to 3 shall be explained below in order.

Method 1:

The specific examples of the acrylic halides used in the method 1 include acrylic chloride, methacrylic chloride, 2-trifluoromethylacrylic chloride, acrylic bromide, methacrylic bromide, 2-trifluoromethylacrylic bromide and the like. Among them, acrylic chloride, methacrylic chloride and 2-trifluoromethylacrylic chloride are preferred from the viewpoint of easier availability.

A use amount of the acrylic halides falls in a range of preferably 1 to 10 times mole based on the alcohol derivative (2), and it falls in a range of more preferably 1 to 5 times mole from the viewpoint of easiness in after-treatment.

The specific examples of the base used in the method 1 shall not specifically be restricted as long as they neutralize by-produced acids and include, for example, nitrogen-containing heterocyclic aromatic compounds such as pyridine, 2-methylpyridine, 2-methyl-5-ethylpyridine, 2,6-dimethylpyridine and the like; amines such as triethylamine, triethylenetetraamine, triethanolamine, piperazine, diazabicyclo[2.2.2]octane and the like; and hydrogencarbonates of alkali metals such as sodium hydrogencarbonate and the like. They may be used alone or in a mixture of two or more kinds thereof.

A use amount of the base falls in a range of preferably 1 to 10 times mole based on the alcohol derivative (2), and it falls in a range of more preferably 1 to 5 times mole from the viewpoint of easiness in after-treatment.

The reaction of the method 1 is carried out in the presence or the absence of a solvent.

The solvent shall not specifically be restricted as long as the reaction is not inhibited, and it includes, for example, saturated hydrocarbon solvents such as hexane, heptane, cyclohexane and the like; aromatic hydrocarbon solvents such as benzene, toluene, xylene and the like; chlorinated hydrocarbon solvents such as methylene chloride, dichloroethane, chlorinated benzene and the like; ether solvents such as diethyl ether, diisopropyl ether, tetrahydrofuran, furan and the like; nitrile solvents such as acetonitrile, benzonitrile the like; ester solvents such as methyl acetate, ethyl acetate, propyl acetate and the like; and ketone base solvents such as 2-butanone, 4-methyl-2-pentanone and the like. The solvent may be used alone or in a mixture of two or more kinds thereof.

When the reaction is carried out in the presence of the solvent, a use amount of the solvent falls in a range of preferably 0.5 to 100 mass times based on the alcohol derivative (2), and it falls in a range of more preferably 0.5 to 20 mass times from the viewpoint of easiness in after-treatment.

A polymerization inhibitor can be used in the reaction of the method 1 in order to prevent polymerization.

The polymerization inhibitor includes, for example, phenol base polymerization inhibitors such as hydroquinone, p-methoxyphenol and the like; amine base polymerization inhibitors such as N,N'-diisopropyl-p-phenylenediamine, N,N'-di-2-naphthyl-p-phenylenediamine, N-phenyl-N'-(1,3-dimethylbutyl)-p-phenylenediamine and the like; and N-oxyl base polymerization inhibitors such as 4-hydroxy-2,2,6,6-tetramethylpiperidine-N-oxyl, 4-acetamide-2,2,6,6-tetramethylpiperidine-N-oxyl and the like. The polymerization inhibitor can be used alone or in a mixture of two or more kinds thereof. When the polymerization inhibitor is used, a use amount thereof shall not specifically be restricted and can suitably be determined.

The method 1 can be carried out as well by adding an activating agent such as 4-dimethylaminopyridine and the like.

A reaction temperature in the method 1 falls, though varied depending on the kinds of the alcohol derivative (2) and the acrylic halides and the presence or the absence of the activating agent used, in a range of preferably about −50 to 100° C., and it falls in a range of more preferably about −30 to 80° C. from the viewpoint of the reaction rate and inhibition of the polymerization. The reaction pressure shall not specifically be restricted, and the reaction is preferably carried out usually under an atmospheric pressure.

A reaction time in the method 1 falls, though varied depending on the kinds and the use amounts of the base, the alcohol derivative (2) and the acrylic halides and the reaction temperature, in a range of preferably about 1 to 50 hours.

The method 1 is preferably carried out under inert gas atmosphere of nitrogen, argon and the like.

A method for carrying out the method 1 shall not specifically be restricted, and preferred is a method in which a reactor is charged with the alcohol derivative (2), the base and, if necessary, the solvent, the polymerization inhibitor and the activating agent and in which the acrylic halides are dropwise added to the above mixed solution under a desired reaction temperature and a desired reaction pressure.

Method 2:

The specific examples of the acrylic anhydrides used in the method 2 include acrylic anhydride, methacrylic anhydride, 2-trifluoromethylacrylic anhydride, acrylic pivalic anhydride, methacrylic pivalic anhydride, 2-trifluoromethylacrylic pivalic anhydride, acrylic methanesulfonic anhydride, methacrylic methanesulfonic anhydride, 2-trifluoromethylacrylic methanesulfonic anhydride and the like.

A use amount of the acrylic anhydrides falls in a range of preferably 1 to 10 times mole based on the alcohol derivative (2), and it falls in a range of more preferably 1 to 5 times mole from the viewpoint of easiness in after-treatment.

The base used in the method 2 includes the same bases as shown as the examples in the method 1. The base may be used alone or in a mixture of two or more kinds thereof. A use amount of the base falls in a range of preferably 1 to 10 times mole based on the alcohol derivative (2), and it falls in a range of more preferably 1 to 5 times mole from the viewpoint of easiness in after-treatment.

The reaction of the method 2 is carried out in the presence or the absence of a solvent.

The solvent shall not specifically be restricted as long as the reaction is not inhibited, and it includes the same solvents as shown as the examples in the method 1. The solvent may be used alone or in a mixture of two or more kinds thereof.

When the reaction is carried out in the presence of the solvent, a use amount of the solvent falls in a range of preferably 0.5 to 100 mass times based on the diene derivative (5), and it falls in a range of more preferably 0.5 to 20 mass times from the viewpoint of easiness in after-treatment.

A polymerization inhibitor can be used in the reaction of the method 2 in order to prevent polymerization. The polymerization inhibitor includes the same polymerization inhibitors as shown as the examples in the method 1. The polymerization inhibitor can be used alone or in a mixture of two or more kinds thereof. When the polymerization inhibitor is used, a use amount thereof shall not specifically be restricted and can suitably be determined.

The method 2 can be carried out as well by adding an activating agent such as 4-dimethylaminopyridine and the like.

A reaction temperature in the method 2 falls, though varied depending on the kinds of the alcohol derivative (2) and the acrylic anhydrides and the presence or the absence of the activating agent used, in a range of preferably about −50 to 100° C., and it falls in a range of more preferably about −30 to 80° C. from the viewpoint of the reaction rate and inhibition of the polymerization. The reaction pressure shall not specifically be restricted, and the reaction is preferably carried out usually under an atmospheric pressure.

A reaction time in the method 2 falls, though varied depending on the kinds and the use amounts of the base, the alcohol derivative (2) and the acrylic anhydrides and the reaction temperature, in a range of preferably about 1 to 50 hours.

The method 2 is preferably carried out under inert gas atmosphere of nitrogen, argon and the like.

Method 3:

The acrylic acids used in the method 3 are acrylic acid, methacrylic acid or 2-trifluoromethylacrylic acid. A use amount of the acrylic acids falls in a range of preferably 1 to 50 times mole based on the alcohol derivative (2), and it falls in a range of more preferably 1 to 20 times mole from the viewpoint of easiness in after-treatment.

Usually, an acid catalyst is used in the method 3. The acid catalyst includes, for example, sulfuric acid, p-toluenesulfonic acid monohydrate and solid acid catalysts such as acidic ion-exchange resins and the like. When the acid catalyst other than the solid acid catalysts is used, a use amount thereof falls in a range of preferably 0.001 to 2 times mole, more preferably 0.01 to 1 time mole based on the alcohol derivative (2). When the solid acid catalyst is used as the acid catalyst, a use amount thereof can suitably be set according to a use amount of the alcohol derivative (2).

A polymerization inhibitor can be used in the reaction of the method 3 in order to prevent polymerization. The polymerization inhibitor includes the same polymerization inhibitors as shown as the examples in the method 1. The polymerization inhibitor can be used alone or in a mixture of two or more kinds thereof. When the polymerization inhibitor is used, a use amount thereof shall not specifically be restricted and can suitably be determined.

A reaction temperature in the method 3 falls, though varied depending on the kinds of the alcohol derivative (2) and the acrylic acids, in a range of preferably about 30 to 150° C., more preferably about 50 to 100° C. The reaction pressure shall not specifically be restricted, and the reaction is preferably carried out usually under an atmospheric pressure.

A reaction time in the method 3 falls, though varied depending on the kinds and the use amounts of the base, the alcohol derivative (2) and the acrylic acids and the reaction temperature, in a range of preferably about 1 to 50 hours.

The reaction in the method 3 is an equilibrium reaction, and therefore it is carried out preferably while removing by-produced water from the reaction system in order to allow the reaction to sufficiently progress. A method for removing water includes, for example, a method in which a solvent such as hexane, toluene and the like forming an azeotropic mixture with water is used to remove water from a device such as a decanter and the like and a method in which a water adsorbent such as a molecular sieve and the like is used.

The acrylate derivative (1) can be separated from the reaction mixture obtained by the method 1, 2 or 3 described above and refined by a method used usually for separating organic compounds, such as extraction by a solvent, distillation and the like. Further, a purity thereof can be enhanced by a method used usually for refining organic compounds, such as recrystallization, distillation, sublimation and the like.

Polymer Compound:

A polymer prepared by polymerizing the acrylate derivative (1) of the present invention alone or a copolymer prepared by copolymerizing the acrylate derivative (1) with other polymerizable compounds is useful as a polymer compound for photoresist compositions.

The specific examples of the other polymerizable compounds (hereinafter referred to as the copolymerization monomers) which can be copolymerized with the acrylate derivative (1) include, for example, compounds represented by chemical formulas shown below, but they shall not specifically be restricted to these compounds.

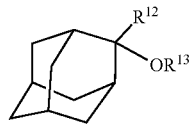 (I)

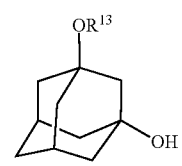 (II)

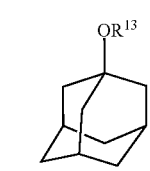 (III)

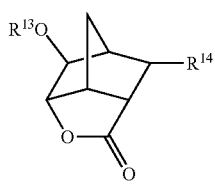 (IV)

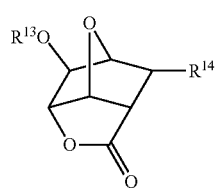 (V)

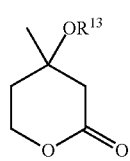 (VI)

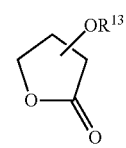 (VII)

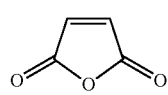 (VIII)

 (IX)

 (X)

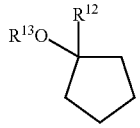 (XI)

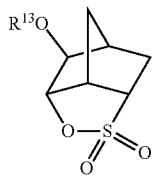 (XII)

In Formulas (I) to (XII) described above, $R^{12}$ represents a hydrogen atom or an alkyl group having 1 to 3 carbon atoms, and $R^{13}$ represents a polymerizable group. $R^{14}$ represents a hydrogen atom or $-COOR^{15}$, and $R^{15}$ represents an alkyl group having 1 to 3 carbon atoms. Also, $R^{16}$ represents an alkyl group.

In the copolymerization monomers, the alkyl group having 1 to 3 carbon atoms each represented independently by $R^{12}$ and $R^{15}$ includes methyl, ethyl, n-propyl and isopropyl. The alkyl group represented by $R^{16}$ includes, for example, methyl, ethyl, n-propyl, isopropyl, n-butyl, isobutyl, s-butyl, t-butyl and the like. The polymerizable group represented by $R^{13}$ includes, for example, acryloyl, methacryloyl, crotonoyl and the like.

The polymer compound can be produced by radical polymerization according to an ordinary process. In particular, living radical polymerization and the like can be listed as a process for synthesizing the polymer compound having a narrow molecular weight distribution.

In a general radical polymerization process, one or more kinds of the acrylate derivative (1) according to necessity and one or more kinds of the foregoing copolymerization monomer according to necessity are polymerized in the presence of a radical polymerization initiator, a solvent and, if necessary, a chain transfer agent.

A method for carrying out the radical polymerization shall not specifically be restricted, and capable of being used are conventional methods used in producing, for example, acryl base polymer compounds, such as a solution polymerization method, an emulsion polymerization method, a suspension polymerization method, a bulk polymerization method and the like.

The radical polymerization initiator described above includes, for example, hydroperoxide compounds such as t-butyl hydroperoxide, cumene hydroperoxide and the like; dialkyl peroxide compounds such as di-t-butyl peroxide, t-butyl-cumyl peroxide, di-α-cumyl peroxide and the like; diacyl peroxide compounds such as benzoyl peroxide, diisobutyryl peroxide and the like; and azo compounds such as 2,2'-azobisisobutyronitrile, dimethyl 2,2'-azobisisobutyrate and the like.

A use amount of the radical polymerization initiator can suitably be selected according to the kinds and the use amounts of the acrylate derivative (1), the copolymerization monomer, the chain transfer agent and the solvent which are used for the polymerization reaction, and it falls usually in a range of preferably 0.005 to 0.2 mole, more preferably 0.01 to 0.15 mole based on 1 mole of the whole polymerizable compounds (a total amounts of the acrylate derivative (1) and the copolymerization monomer; hereinafter the same shall apply).

The chain transfer agent described above includes, for example, thiol compounds such as dodecanethiol, mercaptoethanol, mercaptopropanol, mercaptoacetic acid, mercaptopropionic acid and the like. When the chain transfer agent is used, a use amount thereof falls usually in a range of preferably 0.005 to 0.2 mole, more preferably 0.01 to 0.15 mole based on 1 mole of the whole polymerizable compounds.

The solvent described above shall not specifically be restricted as long as the polymerization reaction is not inhibited, and it includes, for example, glycol ethers such as propylene glycol monoethyl ether, propylene glycol monomethyl ether acetate, ethylene glycol monomethyl ether, ethylene glycol monomethyl ether acetate, ethylene glycol monomethyl ether propionate, ethylene glycol monobutyl ether, ethylene glycol monobutyl ether acetate, diethylene glycol dimethyl ether and the like; esters such as ethyl lactate, methyl 3-methoxypropionate, methyl acetate, ethyl acetate, propyl acetate and the like; ketones such as acetone, methyl ethyl ketone, methyl isopropyl ketone, methyl isobutyl ketone, methyl amyl ketone, cyclopentanone, cyclohexanone and the like; and ethers such as diethyl ether, diisopropyl ether, dibutyl ether, tetrahydrofuran, 1,4-dioxane and the like.

A use amount of the solvent falls in a range of usually 0.5 to 20 parts by mass based on 1 part by mass of the whole polymerizable compounds, and it falls in a range of preferably 1 to 10 parts by mass from the viewpoint of an economical efficiency.

The polymerization temperature is usually 40 to 150° C., and it falls in a range of preferably 60 to 120° C. from the viewpoint of a stability of the polymer compound produced.

Time in the polymerization reaction is varied according to the polymerization conditions such as the kinds and the use amounts of the acrylate derivative (1), the copolymerization monomer, the polymerization initiator and the solvent, a temperature of the polymerization reaction and the like, and it falls usually in a range of preferably 30 minutes to 48 hours, more preferably 1 hour to 24 hours.

The polymer compound thus obtained can be isolated by an ordinary operation such as reprecipitation and the like. The polymer compound isolated can be dried by vacuum drying.

A solvent used in the operation of the reprecipitation includes, for example, aliphatic hydrocarbons such as pentane, hexane and the like; alicyclic hydrocarbons such as cyclohexane and the like; aromatic hydrocarbons such as benzene, xylene and the like; halogenated hydrocarbons such as methylene chloride, chloroform, chlorobenzene, dichlorobenzene and the like; nitrated hydrocarbons such as nitromethane and the like; nitriles such as acetonitrile, benzonitrile and the like; ethers such as diethyl ether, diisopropyl ether, tetrahydrofuran, 1,4-dioxane and the like; ketones such as acetone, methyl ethyl ketone and the like; carboxylic acids such as acetic acid and the like; esters such as ethyl acetate, butyl acetate and the like; carbonates such as dimethyl carbonate, diethyl carbonate, ethylene carbonate and the like; alcohols such as methanol, ethanol, propanol, isopropyl alcohol, butanol and the like; and water.

Photoresist Composition:

A photoresist composition is prepared by blending the polymer compound described above with an organic solvent, an optical acid-generating agent and, if necessary, a basic compound and additives.

Optical acid-generating agents which have so far usually been used for chemical amplification type photoresists can be used as the optical acid-generating agent.

Further, the photoresist composition can be blended with a surfactant, a sensitizer, a halation inhibitor, a form-improving agent, a storage stabilizer, a defoaming agent and the like.

EXAMPLES

The present invention shall specifically be explained with reference to examples, but the present invention shall not be restricted by these examples.

Example 1 First Step

First Step-1:

A three neck flask having an inner content of 2 L equipped with a thermometer, a stirring device, a nitrogen-introducing tube and a dropping funnel was charged with 217.2 g (2.400 mol) of acryloyl chloride and 520 g of toluene, and the inner temperature was lowered to 0° C. Cyclopentadiene 190.4 g (2.880 mol) was dropwise added from the dropping funnel to the above mixed solution in one hour. After finishing dropwise adding, the mixed solution was stirred at 0° C. for one hour to prepare a reaction intermediate solution.

First Step-2:

A three neck flask having an inner content of 2 L equipped with a thermometer, a stirring device, a nitrogen-introducing tube and a dropping funnel was charged with 201.1 g (2.750 mol) of t-butylamine and 513 g of toluene, and the inner temperature was lowered to 0° C. The reaction intermediate solution obtained in the first step-1 described above was dropwise added from the dropping funnel to the above mixed solution in one hour and 30 minutes, and then the inner temperature was elevated up to 25° C.

Ethyl acetate 1800 ml and water 300 ml were added to a reaction mixture obtained, and the mixture was stirred for 30 minutes and then left standing still and separated to thereby obtain an organic layer. The organic layer thus obtained was concentrated under reduced pressure to obtain a concentrate.

Ethyl acetate 750 ml and hexane 250 ml were added to the above concentrate and heated to 40° C. to dissolve the concentrate. The solution was cooled down to 2° C. while stirring, and then crystals deposited were obtained by filtering. The crystals thus obtained were dried under reduced pressure to obtain 124.3 g (0.643 mol; yield: 26.8%) of N-t-butylbicyclo[2.2.1]hepta-5-ene-2-carboxamide having the following characteristics.

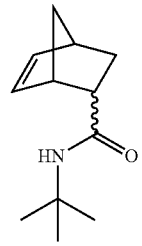

$^1$H-NMR (270 MHz, CDCl$_3$, TMS, ppm) δ: 6.24 (1H, m), 5.97 (1H, m), 5.20 (1H, br), 3.09 (1H, s), 2.90 (1H, s), 2.77 (1H, m), 1.86 (1H, m), 1.42 (1H, m), 1.35 (9H, s), 1.39 to 1.30 (2H, m)

Example 2 Second Step

A three neck flask having an inner content of 2 L equipped with a thermometer, a stirring device, a nitrogen-introducing tube and a dropping funnel was charged with 50.0 g (0.259 mol) of N-t-butylbicyclo[2.2.1]hepta-5-ene-2-carboxamide, 250 g of methylene chloride, 121.6 g (0.880 mol) of potassium carbonate and 550 g of water, and the inner temperature was lowered to 0° C. m-Chloroperbenzoic acid 75.9 g (0.440 mol) and methylene chloride 1559 g were dropwise added from the dropping funnel to the above mixed solution in 20 minutes. The solution was stirred at 0 to 7° C. for 4 hours, and then 22 g of a saturated sodium sulfite aqueous solution was added thereto and stirred for 30 minutes. The solution was left standing still and separated, and then the organic layer was washed twice with 400 ml of water. The organic layer thus obtained was concentrated under reduced pressure to obtain a concentrate.

Diisopropyl ether 554 g and hexane 222 g were added to the above concentrate, and the inner temperature was elevated up to 50° C. to dissolve the concentrate. Then, the solution was cooled down to 2° C., and crystals deposited were obtained by filtering. The crystals thus obtained were dried under reduced pressure to obtain 26.4 g (0.126 mol; yield: 48.6%) of N-t-butyl-5,6-epoxybicyclo[2.2.1]hepta-2-carboxamide having the following characteristics.

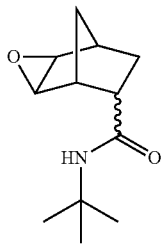

$^1$H-NMR (270 MHz, CDCl$_3$, TMS, ppm) δ: 5.31 (1H, br), 3.12 (2H, m), 2.60 (1H, s), 2.52 (1H, s), 2.04 (1H, m), 1.92 (1H, m), 1.59 (1H, m), 1.35 (9H, s), 1.39 to 1.30 (2H, m)

Comparative Example 1

An experiment was carried out in the same manner, except that in Example 2, 121.6 g (0.880 mol) of potassium carbonate was not used, and only 0.5 g (0.002 mol; yield: 0.8%) of N-t-butyl-5,6-epoxybicyclo[2.2.1]hepta-2-carboxamide was obtained.

Example 3 Third Step

A three neck flask having an inner content of 2 L equipped with a thermometer, a stirring device, a nitrogen-introducing tube and a dropping funnel was charged with 61.0 g (0.544 mol) of potassium t-butoxide and 1045 g of t-butanol, and the solution was heated up to 50° C. N-t-butyl-5,6-epoxybicyclo[2.2.1]hepta-2-carboxamide 56.9 g (0.272 mol) was added to the above mixed solution in one hour. Subsequently, the inner temperature was lowered down to 25° C., and then 620 g of 3.9 mass % hydrochloric acid and 1900 ml of ethyl acetate were added thereto and stirred for 30 minutes. The solution was left standing still and separated, and then the organic layer was washed twice with 400 ml of water. The organic layer thus obtained was concentrated under reduced pressure to obtain a concentrate.

Methanol 30 g and diisopropyl ether 820 g were added to the concentrate obtained, and the inner temperature was elevated up to 50° C. to dissolve the concentrate. Subsequently, the solution was cooled down to 0° C., and then crude crystals deposited were obtained by filtering. Ethyl acetate 200 g and diisopropyl ether 200 g were added to the crude crystals thus obtained, and the inner temperature was elevated up to 50° C. to dissolve the crude crystals. Subsequently, the solution was cooled down to 0° C., and then crystals deposited were obtained by filtering. The crystals thus obtained were dried under reduced pressure to obtain 24.9 g (0.119 mol; yield: 43.8%) of N-t-butyl-6-hydroxyhexahydro-2-oxo-3,5-methanol-4H-cyclopenta[2,3-b]pyrrole having the following characteristics.

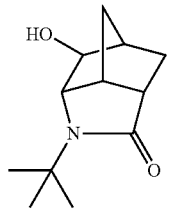

$^1$H-NMR (270 MHz, CDCl$_3$, TMS, ppm) δ: 3.63 (1H, s), 3.55 (1H, m), 2.85 (1H, m), 2.44 (1H, br), 2.35 (1H, m), 2.25 (1H, m), 2.00 to 2.78 (2H, m), 1.42 (9H, s), 1.50 to 1.35 (2H, m)

Example 4 Fourth Step

Method 1)

A three neck flask having an inner content of 500 mL equipped with a thermometer, a stirring device, a nitrogen-introducing tube and a dropping funnel was charged with 34.1 g (0.163 mol) of N-t-butyl-6-hydroxyhexahydro-2-oxo-3,5-methanol-4H-cyclopenta[2,3-b]pyrrole, 340 ml of methylene chloride and 29.8 g (0.294 mol) of triethylamine, and the inner temperature was lowered down to −40° C. Methacrylic chloride 20.5 g (0.196 mol) was dropwise added from the dropping funnel to the above mixed solution in one hour. Methanol 12 ml was added to the above reaction mixture, and subsequently 120 ml of water was added thereto, followed by stirring the mixture for 30 minutes. The solution was left standing still and separated, and then the aqueous layer was extracted four times with 50 ml of methylene chloride. The methylene chloride layers obtained were put together and concentrated under reduced pressure.

The concentrate thus obtained was refined by silica gel chromatography to obtain 17.2 g (0.062 mol; yield: 38.0%) of N-t-butylhexahydro-2-oxo-3,5-methanol-4H-cyclopenta[2,3-b]pyrrole-6-yl=methacrylic acid having the following characteristics.

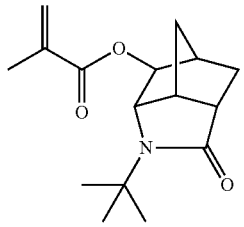

$^1$H-NMR (270 MHz, CDCl$_3$, TMS, ppm) δ: 6.11 (1H, s), 5.59 (1H, m), 4.67 (1H, m), 3.70 (1H, m), 2.93 (1H, m), 2.51 (1H, m), 2.32 (1H, m), 1.95 (3H, s), 1.90 (1H, m), 1.85 (1H, m), 1.64 (1H, m), 1.47 (1H, m), 1.40 (9H, s)

Reference Example

Monomers (1) to (7) represented by the following chemical formulas were used to synthesize polymer compounds shown below:

monomer (1)

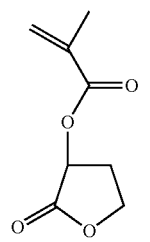

monomer (2)

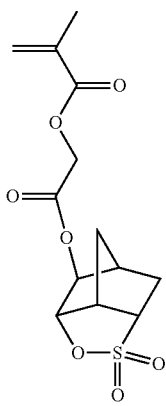

monomer (3)

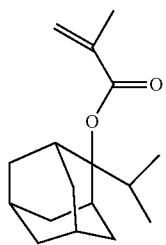

monomer (4)

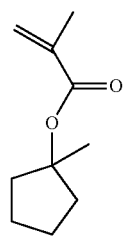

monomer (5)

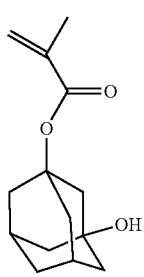

monomer (6)

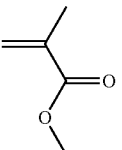

monomer (7)

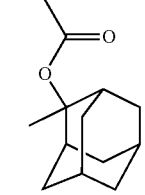

The monomer (2) was synthesized by a method shown below.

Synthesis of Monomer (2):

A three neck flask having an inner content of 500 mL was charged with 20 g (105.14 mmol) of alcohol shown in the following chemical reaction equation, 30.23 g (157.71 mmol) of ethyldiisopropylaminocarbodiimide hydrochloride and 300 ml of a tetrahydrofuran (THF) solution of 0.6 g (5 mmol) of dimethylaminopyridine in nitrogen atmosphere. A carboxylic acid compound 16.67 g (115.66 mmol) shown in the following chemical reaction equation was added thereto while cooling on ice, and then the mixture was stirred at room temperature for 12 hours.

After adding 50 ml of water to terminate the reaction, the reaction solvent was concentrated under reduced pressure, and the concentrate was extracted three times with ethyl acetate to obtain an organic layer. The organic layer thus obtained was washed in order with water, saturated sodium hydrogencarbonate and a hydrochloric acid aqueous solution having a concentration of 1 mol/L. A product obtained by removing the solvent by distillation under reduced pressure was dried to obtain the monomer (2).

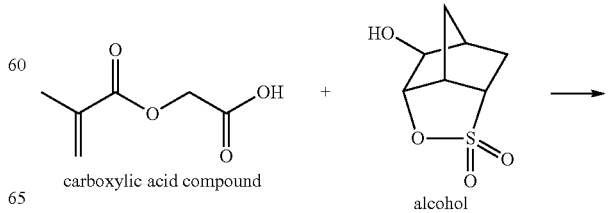

carboxylic acid compound     alcohol

-continued

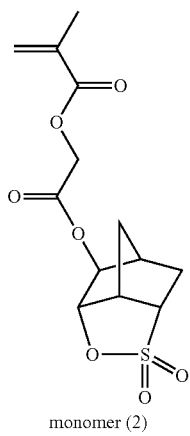

monomer (2)

Synthesis of Polymer Compound (A)-1:

A three neck flask equipped with a thermometer and a reflux condenser was charged with 11.77 g (69.23 mmol) of the monomer (1), 15.00 g (47.47 mmol) of the monomer (2), 16.58 g (63.29 mmol) of the monomer (3), 4.65 g (27.96 mmol) of the monomer (4), 3.27 g (13.85 mmol) of the monomer (5) and 0.55 g (1.98 mmol) of the monomer (7), and they were dissolved in 76.91 g of methyl ethyl ketone to obtain a monomer mixture.

Dimethyl azobisisobutyrate (22.1 mmol) as a polymerization initiator was added to the monomer mixture obtained above and dissolved therein. The mixed solution thus obtained was dropwise added to 42.72 g of methyl ethyl ketone heated to 78° C. in 3 hours under nitrogen atmosphere. After finishing dropwise adding, the reaction solution was heated and stirred for 4 hours, and then it was cooled down to room temperature.

The polymerization solution obtained above was dropwise added to a large amount of n-heptane to deposit a polymer, and white powder precipitated was removed by filtering and washed with a n-heptane/isopropyl alcohol mixed solvent. Then, it was dried to obtain 43 g of a polymer compound (A)-1.

A weight average molecular weight (Mw), a molecular weight dispersion degree (Mw/Mn) and a copolymer composition ratio (a proportion (mole ratio) of the respective structural units in the polymer compound) determined by $^{13}$C-NMR (600 MHz) in the above polymer compound (A)-1 are shown in Table 1.

Synthesis of Polymer Compounds (A)-2 to (A)-6:

An experiment was carried out in the same manner to thereby synthesize polymer compounds (A)-2 to (A)-6, except that in the synthesis of the polymer compound (A)-1 described above, the proportions of the structural units in the respective polymer compounds were changed as shown in Table 1. The weight average molecular weights (Mw) and the molecular weight dispersion degrees (Mw/Mn) of the polymer compounds (A)-2 to (A)-6 are shown in Table 1.

Synthesis of Polymer Compound (A)-7:

A three neck flask equipped with a thermometer and a reflux condenser was charged with 32.32 g (102.29 mmol) of the monomer (2), 11.93 g (34.10 mmol) of the monomer (6), 8.05 g (34.10 mmol) of the monomer (5) and 0.95 g (3.41 mmol) of the monomer (7), and they were dissolved in 106.77 g of methyl ethyl ketone to obtain a mixed solution.

Dimethyl azobisisobutyrate (17.3 mmol) as a polymerization initiator was added to the monomer mixed solution obtained above and dissolved therein. The mixed solution thus obtained was dropwise added to 67.00 g (67.1 g (255.73 mmol) of the monomer (3) was dissolved in advance) of methyl ethyl ketone heated to 80° C. in 3 hours under nitrogen atmosphere. After finishing dropwise adding, the reaction solution was heated and stirred for 2 hours, and then it was cooled down to room temperature.

The polymerization solution obtained above was dropwise added to a large amount of n-heptane to deposit a polymer, and white powder precipitated was removed by filtering and washed with a n-heptane/2-propanol mixed solvent and methanol. Then, it was dried to obtain 65 g of a polymer compound (A)-7.

A weight average molecular weight (Mw), a molecular weight dispersion degree (Mw/Mn) and a copolymer composition ratio (a proportion (mole ratio) of the respective structural units in the polymer compound) determined by $^{13}$C-NMR measurement (600 MHz) in the above polymer compound (A)-1 are shown in Table 1.

Synthesis of Polymer Compounds (A)-8 to (A)-12:

An experiment was carried out in the same manner to thereby synthesize polymer compounds (A)-8 to (A)-12, except that in the synthesis of the polymer compound (A)-7 described above, the proportions of the structural units in the respective polymer compounds were changed as shown in Table 1. The weight average molecular weights (Mw) and the molecular weight dispersion degrees (Mw/Mn) of the polymer compounds (A)-8 to (A)-12 are shown in Table 1.

TABLE 1

| | | proportion of structural units derived from respective monomers (mole %) Monomers | | | | | | | | Mw/ |
|---|---|---|---|---|---|---|---|---|---|---|
| | | (1) | (2) | (3) | (4) | (5) | (6) | (7) | Mw | Mn |
| polymer compound | A-1 | 35 | 22 | 16 | 14 | 12 | — | 1 | 6900 | 1.73 |
| | A-2 | 34 | 20 | 16 | 13 | 11 | — | 6 | 7400 | 1.77 |
| | A-3 | 33 | 19 | 14 | 13 | 11 | — | 10 | 6600 | 1.67 |
| | A-4 | 28 | 18 | 13 | 11 | 9 | — | 21 | 6700 | 1.64 |
| | A-5 | 24 | 15 | 11 | 9 | 8 | — | 33 | 7500 | 1.78 |
| | A-6 | 36 | 22 | 16 | 14 | 12 | — | — | 6700 | 1.69 |
| | A-7 | — | 34 | 43 | — | 11 | 11 | 1 | 8600 | 1.64 |
| | A-8 | — | 33 | 42 | — | 10 | 10 | 5 | 9200 | 1.72 |
| | A-9 | — | 32 | 39 | — | 10 | 10 | 9 | 8900 | 1.69 |
| | A-10 | — | 28 | 34 | — | 9 | 9 | 20 | 9400 | 1.83 |
| | A-11 | — | 21 | 26 | — | 7 | 7 | 39 | 9600 | 1.81 |
| | A-12 | — | 35 | 43 | — | 11 | 11 | — | 8300 | 1.66 |

Synthesis of Fluorine-Containing Polymer Compound (C)-1:

A three neck flask equipped with a thermometer and a reflux condenser was charged with 15.00 g (54.32 mmol) of the monomer (c1) and 5.21 g (23.28 mmol) of the monomer (c2), and they were dissolved in 114.52 g of THF to obtain a monomer mixed solution.

Dimethyl azobisisobutyrate (4.66 mmol) as a polymerization initiator was added to the monomer mixed solution obtained above and dissolved therein. The mixed solution thus obtained was heated and stirred at 80° C. for 6 hours under nitrogen atmosphere, and then it was cooled down to room temperature.

The polymerization solution obtained above was concentrated under reduced pressure and then dropwise added to a large amount of n-heptane to deposit a polymer, and the polymer precipitated was removed by filtering, washed and dried to obtain 5.6 g of a fluorine-containing polymer compound (C)-1.

The above fluorine-containing polymer compound (C)-1 had a weight average molecular weight (Mw) of 25000 and a molecular weight dispersion degree (Mw/Mn) of 1.5. Further, the copolymer composition ratio (a proportion (mole ratio) of the respective structural units in the polymer compound) determined by $^{13}$C-NMR measurement (600 MHz) was l/m=80/20.

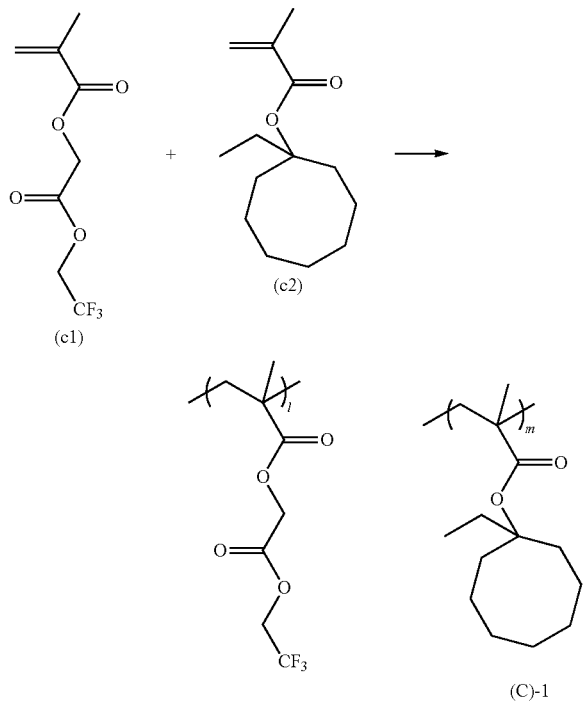

Preparation of Resist Compositions:

The respective components shown in Tables 2 to 3 were mixed and dissolved to prepare resist compositions of a positive type.

TABLE 2

| Resist compo- sition | (A) | (B) | (C) | (D) | (E) | (S) | |
|---|---|---|---|---|---|---|---|
| 1 | (A)-1 [100] | (B)-1 [6.7] | (B)-4 [2.6] | (C)-1 [3.0] | — | (E)-1 [0.75] | (S)-1 [10] | (S)-2 [2800] |
| 2 | (A)-2 [100] | (B)-1 [6.7] | (B)-4 [2.6] | (C)-1 [3.0] | — | (E)-1 [0.75] | (S)-1 [10] | (S)-2 [2800] |
| 3 | (A)-3 [100] | (B)-1 [6.7] | (B)-4 [2.6] | (C)-1 [3.0] | — | (E)-1 [0.75] | (S)-1 [10] | (S)-2 [2800] |
| 4 | (A)-4 [100] | (B)-1 [6.7] | (B)-4 [2.6] | (C)-1 [3.0] | — | (E)-1 [0.75] | (S)-1 [10] | (S)-2 [2800] |
| 5 | (A)-2 [100] | (B)-2 [6.4] | (B)-4 [2.6] | (C)-1 [3.0] | — | (E)-1 [0.75] | (S)-1 [10] | (S)-2 [2800] |
| 6 | (A)-2 [100] | (B)-3 [11.0] | (B)-4 [2.6] | (C)-1 [3.0] | — | (E)-1 [0.75] | (S)-1 [10] | (S)-2 [2800] |
| 7 | (A)-2 [100] | (B)-1 [6.7] | (B)-4 [2.6] | (C)-2 [1.5] | — | (E)-1 [0.75] | (S)-1 [10] | (S)-2 [2800] |
| 8 | (A)-2 [100] | (B)-1 [6.7] | (B)-4 [2.6] | (C)-3 [3.0] | — | (E)-1 [0.75] | (S)-1 [10] | (S)-2 [2800] |
| 9 | (A)-4 [5] (A)-6 [95] | (B)-1 [6.7] | (B)-4 [2.6] | (C)-1 [3.0] | — | (E)-1 [0.75] | (S)-1 [10] | (S)-2 [2800] |
| 10 | (A)-4 [20] (A)-6 [80] | (B)-1 [6.7] | (B)-4 [2.6] | (C)-1 [3.0] | — | (E)-1 [0.75] | (S)-1 [10] | (S)-2 [2800] |

TABLE 2-continued

| Resist compo- sition | (A) | (B) | (C) | (D) | (E) | (S) | |
|---|---|---|---|---|---|---|---|
| 11 | (A)-6 [100] | (B)-1 [6.7] | (B)-4 [2.6] | (C)-1 [3.0] | — | (E)-1 [0.75] | (S)-1 [10] | (S)-2 [2800] |
| 12 | (A)-6 [100] | (B)-1 [6.7] | (B)-4 [2.6] | (C)-1 [3.0] | (D)-1 [0.60] | (E)-1 [0.75] | (S)-1 [10] | (S)-2 [2800] |
| 13 | (A)-6 [100] | (B)-1 [6.7] | (B)-4 [2.6] | (C)-1 [3.0] | (D)-2 [0.39] | (E)-1 [0.75] | (S)-1 [10] | (S)-2 [2800] |
| 14 | (A)-6 [100] | (B)-1 [6.7] | (B)-4 [2.6] | (C)-1 [3.0] | (D)-3 [0.53] | (E)-1 [0.75] | (S)-1 [10] | (S)-2 [2800] |
| 15 | (A)-5 [100] | (B)-1 [6.7] | (B)-4 [2.6] | (C)-1 [3.0] | — | (E)-1 [0.75] | (S)-1 [10] | (S)-2 [2800] |

The numerical values in an inside of [ ] in Table 2 show the blend amounts (parts by mass). Further, the signals in Table 2 show the following ones respectively:

(A)-1: polymer compound (A)-1
(A)-2: polymer compound (A)-2
(A)-3: polymer compound (A)-3
(A)-4: polymer compound (A)-4
(A)-5: polymer compound (A)-5
(A)-6: polymer compound (A)-6
(B)-1: compound represented by a chemical formula (B)-1 shown below
(B)-2: compound represented by a chemical formula (B)-2 shown below
(B)-3: compound represented by a chemical formula (B)-3 shown below
(B)-4: compound represented by a chemical formula (B)-4 shown Below
(C)-1: fluorine-containing polymer compound (C)-1
(C)-2: fluorine-containing polymer compound (C)-2 represented by a chemical formula (C)-2 shown below (synthesized by a method described in Japanese Patent Application Laid-Open No. 134607/2008; Mw=8000, Mw/Mn=1.39, composition ratio: l/m=54.2/45.8 (mole ratio))
(D)-1: tri-n-pentylamine
(D)-2: triethanolamine
(D)-3: compound represented by a chemical formula (D)-3 shown below
(E)-1: salicylic acid
(S)-1: γ-butyrolactone
(S)-2: mixed solvent of propylene glycol monomethyl ether acetate/propylene glycol monomethyl ether/cyclohexanone=45/30/25 (mass ratio)

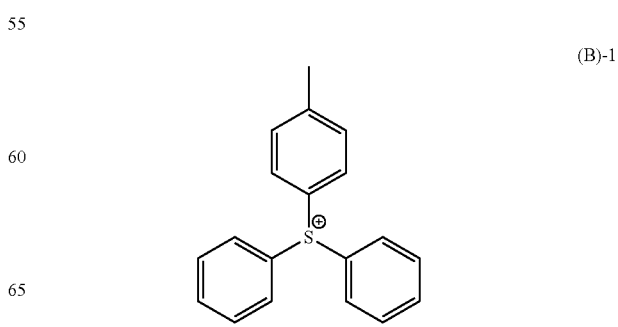

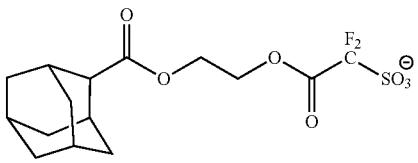
(B)-2
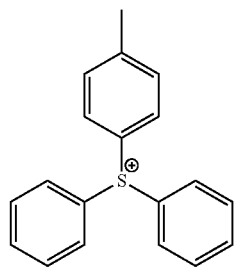
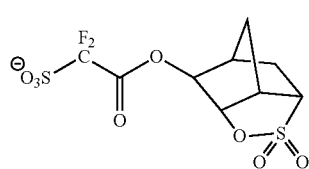
(B)-3
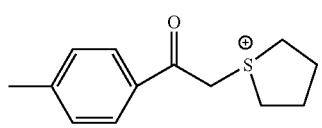
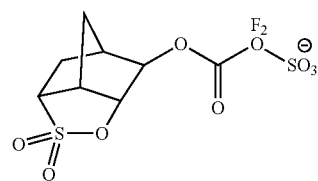
(B)-4
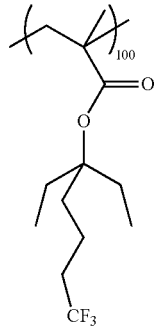 (C)-2
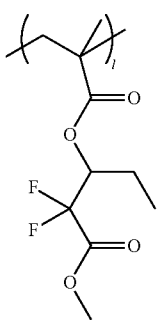 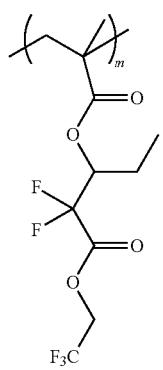 (C)-3
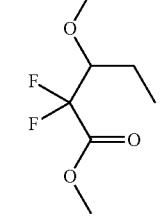 (D)-3
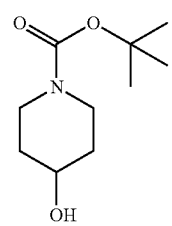
TABLE 3
| Resist compo- sition | Components | | | | | | |
|---|---|---|---|---|---|---|---|
| | (A) | (B) | | (C) | (D) | (E) | (S) |
| 16 | (A)-7 | (B)-2 | (B)-4 | (C)-1 | — | (E)-1 | (S)-1 (S)-3 |
| | [100] | [8.3] | [1.3] | [3.0] | | [0.5] | [10] [2900] |
| 17 | (A)-8 | (B)-2 | (B)-4 | (C)-1 | — | (E)-1 | (S)-1 (S)-3 |
| | [100] | [8.3] | [1.3] | [3.0] | | [0.5] | [10] [2900] |
| 18 | (A)-9 | (B)-2 | (B)-4 | (C)-1 | — | (E)-1 | (S)-1 (S)-3 |
| | [100] | [8.3] | [1.3] | [3.0] | | [0.5] | [10] [2900] |
| 19 | (A)-10 | (B)-2 | (B)-4 | (C)-1 | — | (E)-1 | (S)-1 (S)-3 |
| | [100] | [8.3] | [1.3] | [3.0] | | [0.5] | [10] [2900] |
| 20 | (A)-8 | (B)-5 | (B)-4 | (C)-1 | — | (E)-1 | (S)-1 (S)-3 |
| | [100] | [8.0] | [1.3] | [3.0] | | [0.5] | [10] [2900] |
| 21 | (A)-8 | (B)-6 | (B)-4 | (C)-1 | — | (E)-1 | (S)-1 (S)-3 |
| | [100] | [7.8] | [1.3] | [3.0] | | [0.5] | [10] [2900] |
| 22 | (A)-8 | (B)-3 | — | (C)-1 | — | (E)-1 | (S)-1 (S)-3 |
| | [100] | [15.0] | | [3.0] | | [0.5] | [10] [2900] |
| 23 | (A)-8 | (B)-2 | (B)-4 | (C)-2 | — | (E)-1 | (S)-1 (S)-3 |
| | [100] | [8.3] | [1.3] | [1.5] | | [0.5] | [10] [2900] |
| 24 | (A)-8 | (B)-2 | (B)-4 | (C)-3 | — | (E)-1 | (S)-1 (S)-3 |
| | [100] | [8.3] | [1.3] | [3.0] | | [0.5] | [10] [2900] |
| 25 | (A)-12 | (B)-2 | (B)-4 | (C)-1 | — | (E)-1 | (S)-1 (S)-3 |
| | [100] | [8.3] | [1.3] | [3.0] | | [0.5] | [10] [2900] |

TABLE 3-continued

| Resist compo-sition | Components | | | | | | |
|---|---|---|---|---|---|---|---|
| | (A) | (B) | | (C) | (D) | (E) | (S) |
| 26 | (A)-12 [100] | (B)-2 [8.3] | (B)-4 [1.3] | (C)-1 [3.0] | (D)-1 [0.25] | (E)-1 [0.5] | (S)-1 [10] (S)-3 [2900] |
| 27 | (A)-12 [100] | (B)-2 [8.3] | (B)-4 [1.3] | (C)-1 [3.0] | (D)-2 [0.16] | (E)-1 [0.5] | (S)-1 [10] (S)-3 [2900] |
| 28 | (A)-12 [100] | (B)-2 [8.3] | (B)-4 [1.3] | (C)-1 [3.0] | (D)-3 [0.22] | (E)-1 [0.5] | (S)-1 [10] (S)-3 [2900] |
| 29 | (A)-11 [100] | (B)-2 [8.3] | (B)-4 [1.3] | (C)-1 [3.0] | — | (E)-1 [0.5] | (S)-1 [10] (S)-3 [2900] |

The numerical values in an inside of [ ] in Table 2 show the blend amounts (parts by mass). Further, the signals in Table 2 show the following ones respectively. The same signals as in Table 1 are described in the remarks of Table 1.

(A)-7: polymer compound (A)-7
(A)-8: polymer compound (A)-8
(A)-9: polymer compound (A)-9
(A)-10: polymer compound (A)-10
(A)-11: polymer compound (A)-11
(A)-12: polymer compound (A)-12
(B)-5: compound represented by a chemical formula (B)-5 shown below
(B)-6: compound represented by a chemical formula (B)-6 shown below
(S)-3: mixed solvent of propylene glycol monomethyl ether acetate/propylene glycol monomethyl ether=6/4 (mass ratio)

(B)-5

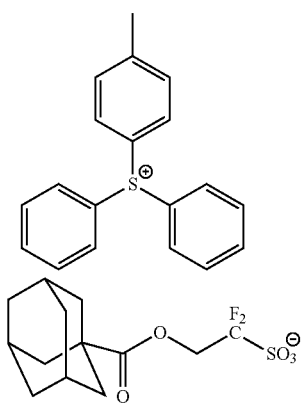

(B)-6

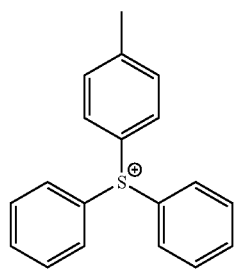

-continued

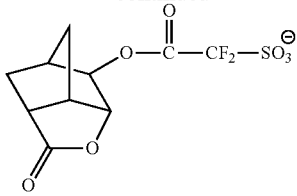

<Evaluation (1) of Lithographic Performance>

The resist compositions 1 to 14 described above were used to prepare resist patterns by a resist pattern-forming method shown below and evaluate the lithographic performance.

Formation of Resist Patterns:

An organic anti reflective coat composition "ARC95" (manufactured by Brewer Science, Inc.) was coated on a silicon wafer of 12 inch by means of a spinner, and it was dried by calcining at 205° C. for 60 seconds on a hot plate to thereby form an organic anti reflective coat having a film thickness of 90 nm.

Then, each of the resist compositions 1 to 14 was coated on the above organic anti reflective coat by means of a spinner, and it was subjected to post applying baking (PAB) treatment on the conditions of 120° C. and 60 seconds and dried on a hot plate to thereby form a resist film having a film thickness of 95 nm.

Next, the resist film described above was exposed selectively with an ArF excimer laser (193 nm) via a mask pattern (6% halftone) by means of an ArF immersion exposing equipment "NSR-S609B" (NA (numerical aperture)=1.07, Cross pole, immersion medium: water, manufactured by Nikon Corporation).

Then, it was subjected to post exposure bake (PEB) treatment at 95° C. for 60 seconds and further subjected to alkali developing treatment at 23° C. for 10 seconds with a 2.38 mass % tetramethylammonium hydroxide aqueous solution, and then it was rinsed with purified water for 30 seconds and subjected to shaking drying.

As a result thereof, 1:1 line & space (L/S) patterns having a line width of 50 nm were obtained in all examples. An optimum exposure value Eop (mJ/cm$^2$) in which the above L/S pattern was formed was determined and set to a barometer of the sensitivity. The results thereof are shown in Table 4.

Evaluation of Depth of Focus (DOF):

In Eop described above, the focal point was suitably moved upward and downward to determine the depth of focus (unit: μm) which could be given by the 1:1 L/S pattern of 1:1 described above in a range of a dimensional change rate of a target dimension 50 nm±5% (that is, 47.5 to 52.5 nm). The results thereof are shown in Table 4.

Evaluation of LWR:

In the 1:1 L/S patterns of 1:1 given by Eop described above, line widths were measured at 50 points in a longitudinal direction of the lines by means of length measurement SEM "S-9380" (scanning electron microscope, accelerating voltage: 300 V, manufactured by Hitachi, Ltd.), and a three times value (3s) of the standard deviation (s) was calculated as a scale showing LWR from the above result. The results thereof are shown in Table 4.

The smaller value of above 3s means that a roughness of the line width is smaller and that the L/S patterns having a more uniform width are obtained.

TABLE 4

| Resist composition | PAB/PEB (° C.) | Sensitivity (mJ/cm$^2$) | DOF (μm) | LWR (nm) |
|---|---|---|---|---|
| 1 | 120/95 | 20 | 0.33 | 5.71 |
| 2 | 120/95 | 37 | 0.34 | 5.58 |
| 3 | 120/95 | 62 | 0.30 | 5.63 |
| 4 | 120/95 | 96 | 0.27 | 5.56 |
| 5 | 120/95 | 46 | 0.31 | 5.31 |
| 6 | 120/95 | 51 | 0.30 | 4.89 |
| 7 | 120/95 | 35 | 0.32 | 5.65 |
| 8 | 120/95 | 35 | 0.33 | 5.44 |
| 9 | 120/95 | 23 | 0.33 | 7.92 |
| 10 | 120/95 | 20 | 0.34 | 5.90 |
| 11 | 120/95 | 12 | 0.33 | 8.76 |
| 12 | 120/95 | 38 | 0.27 | 5.62 |
| 13 | 120/95 | 42 | 0.18 | 6.90 |
| 14 | 120/95 | 56 | 0.34 | 6.71 |

It could be confirmed from the results shown above that the resist compositions 1 to 10 obtained by making use of the acrylate derivative (1) according to the present invention were good in both DOF and LWR and excellent in lithographic performance as compared with the resist compositions 11 to 14 contrary to the above and that they could give resist patterns having a good shape.

<Evaluation (2) of Lithographic Performance>

The resist compositions 16 to 28 described above were used to prepare resist patterns by a resist pattern-forming method shown below and evaluate the lithographic performance.

Formation of Resist Patterns:

An organic anti reflective coat composition "ARC29A" (manufactured by Brewer Science, Inc.) was coated on a silicon wafer of 12 inch by means of a spinner, and it was dried by calcining at 205° C. for 60 seconds on a hot plate to thereby form an organic anti reflective coat having a film thickness of 89 nm.

Then, each of the resist compositions 16 to 28 was coated on the above organic anti reflective coat by means of a spinner, and it was subjected to post apply bake (PAB) treatment on the conditions of 90° C. and 60 seconds and dried on a hot plate to thereby form a resist film having a film thickness of 100 nm.

Next, the resist film described above was irradiated selectively with an ArF excimer laser (193 nm) via a mask pattern (6% halftone) by means of an ArF immersion exposing equipment "NSR—S609B" (NA (numerical aperture)=1.07, Conventional (0.97) w/o POLA NO, immersion medium: water, manufactured by Nikon Corporation).

Then, it was subjected to post exposure bake (PEB) treatment at 80° C. for 60 seconds and further subjected to alkali developing treatment at 23° C. for 20 seconds with a 2.38 mass % tetramethylammonium hydroxide aqueous solution, and then it was rinsed with purified water for 30 seconds and subjected to shaking drying.

As a result thereof, dense contact hole patterns (CH patterns) in which holes having a hole diameter of 90 nm were arranged at an equal space (pitch: 140 nm) were obtained in all examples. An optimum exposure value Eop (mJ/cm$^2$; sensitivity) in which the above CH pattern was formed was determined and set to a barometer of the sensitivity. The results thereof are shown in Table 5.

Evaluation of CDU:

In the CH patterns given in Eop described above, the diameters (CD) of 100 holes in the respective CH patterns were measured, and a three times value (3s) of the standard deviation (s) was calculated as a scale showing a CD uniformity (CDU) from the above result. The results thereof are shown in Table 5.

The smaller value of above 3s means that a critical dimensional uniformity of the hole is higher.

Evaluation of Roundness:

The CH patterns given in Eop described above were observed from an upper side to measure distances from a center of 100 holes to an outer edge thereof in 24 directions in the respective CH patterns by means of length measurement SEM "S-9380" (manufactured by Hitachi, Ltd.), and a three times value (3s) of the standard deviation (s) calculated from the above result was calculated as a scale showing the roundness. The results thereof are shown in Table 5.

The smaller value of above 3s means that a roundness of the holes is higher.

TABLE 5

| Resist composition | PAB/PEB (° C) | Sensitivity (mJ/cm$^2$) | CDU | Roundness |
|---|---|---|---|---|
| 16 | 90/80 | 29 | 7.1 | 7.3 |
| 17 | 90/80 | 48 | 6.9 | 6.6 |
| 18 | 90/80 | 76 | 6.3 | 5.6 |
| 19 | 90/80 | 113 | 6.7 | 6.8 |
| 20 | 90/80 | 41 | 6.6 | 6.1 |
| 21 | 90/80 | 44 | 6.9 | 7.0 |
| 22 | 90/80 | 67 | 6.6 | 6.9 |
| 23 | 90/80 | 28 | 6.6 | 7.0 |
| 24 | 90/80 | 29 | 6.3 | 6.9 |
| 25 | 90/80 | 19 | 8.9 | 9.2 |
| 26 | 90/80 | 41 | 7.5 | 7.7 |
| 27 | 90/80 | 44 | 7.9 | 8.1 |
| 28 | 90/80 | 55 | 8.0 | 7.8 |

It could be confirmed from the results shown above that the resist compositions 16 to 24 obtained by making use of the acrylate derivative (1) according to the present invention had a good CDU and a high roundness and therefore were excellent in lithographic performance as compared with the resist compositions 25 to 28 contrary to the above and that they could give resist patterns having a good shape.

INDUSTRIAL APPLICABILITY

The acrylate derivative (1) of the present invention is excellent in lithographic performance and useful as a raw material of a polymer compound for resist compositions which give resist patterns having a good shape. Further, the alcohol derivative (2) of the present invention is useful as a synthetic intermediate for the above acrylate derivative (1).

What is claimed is:

1. An acrylate derivative represented by Formula (1) shown below:

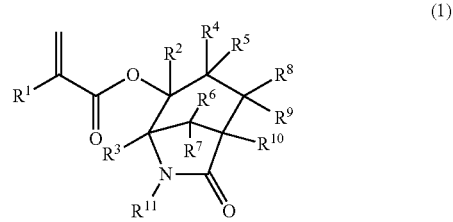

(1)

(wherein R$^1$ represents a hydrogen atom, methyl or trifluoromethyl; R$^2$, R$^3$, R$^5$, R$^7$, R$^8$, R$^9$ and R$^{10}$ each represent independently a hydrogen atom, an alkyl group having 1 to 6 carbon atoms, a cycloalkyl group having 3 to 6 carbon atoms or an alkoxy group having 1 to 6 carbon atoms; $R^4$ and $R^6$ each represent independently a hydrogen atom, an alkyl group having 1 to 6 carbon atoms, a cycloalkyl group having 3 to 6 carbon atoms or an alkoxy group having 1 to 6 carbon atoms, or both of $R^4$ and $R^6$ are combined to represent an alkylene group having 1 to 3 carbon atoms, —O— or —S—; and $R^{11}$ represents a hydrogen atom, an alkyl group having 1 to 6 carbon atoms or a cyclic hydrocarbon group having 3 to 10 carbon atoms).

2. A production process for an acrylate derivative represented by Formula (1) shown below:

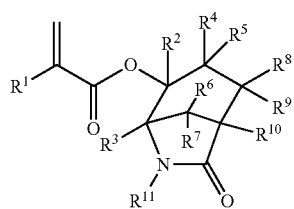

(1)

(wherein $R^1, R^2, R^3, R^4, R^5, R^6, R^7, R^8, R^9, R^{10}$ and $R^{11}$ are the same as defined above), characterized by esterifying an alcohol derivative represented by Formula (2) shown below:

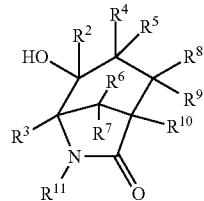

(2)

(wherein $R^2, R^3, R^4, R^5, R^6, R^7, R^8, R^9, R^{10}$ and $R^{11}$ are the same as defined above).

3. A production process for an acrylate derivative represented by Formula (1) shown below:

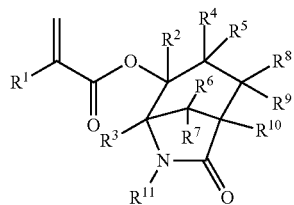

(1)

(wherein $R^1, R^2, R^3, R^4, R^5, R^6, R^7, R^8, R^9, R^{10}$ and $R^{11}$ are the same as defined above), comprising oxidizing a cyclohexene derivative represented by Formula (3) shown below:

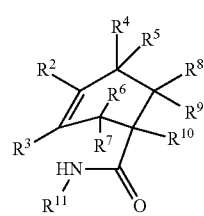

(3)

(wherein $R^2, R^3, R^4, R^5, R^6, R^7, R^8, R^9, R^{10}$ and $R^{11}$ are the same as defined above) in the presence of a base to obtain an epoxy derivative represented by Formula (4) shown below:

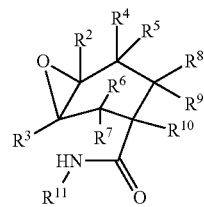

(4)

(wherein $R^2, R^3, R^4, R^5, R^6, R^7, R^8, R^9, R^{10}$ and $R^{11}$ are the same as defined above) and subjecting the above epoxy derivative obtained to base treatment, and esterifying an alcohol derivative, which is obtained by the base treatment, represented by Formula (2) shown below:

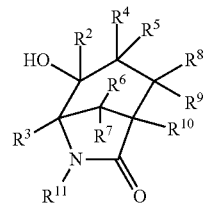

(2)

(wherein $R^2, R^3, R^4, R^5, R^6, R^7, R^8, R^9, R^{10}$ and $R^{11}$ are the same as defined above).

* * * * *